US011439347B2

(12) United States Patent
Fearn et al.

(10) Patent No.: US 11,439,347 B2
(45) Date of Patent: Sep. 13, 2022

(54) PORTABLE DEHYDRATION MONITORING SYSTEM

(71) Applicant: 11 Health & Technologies Limited, Radlett (GB)

(72) Inventors: Robert I. Fearn, Irvine, CA (US); Phillip Edward Mohsien Daneshyar, Mappleborough Green (GB)

(73) Assignee: 11 Health & Technologies Limited, Radlett (GB)

( * ) Notice: Subject to any disclaimer, the term of this patent is extended or adjusted under 35 U.S.C. 154(b) by 236 days.

(21) Appl. No.: 16/882,501

(22) Filed: May 24, 2020

(65) Prior Publication Data
US 2020/0367817 A1  Nov. 26, 2020

Related U.S. Application Data

(60) Provisional application No. 62/852,874, filed on May 24, 2019.

(51) Int. Cl.
*A61B 6/00* (2006.01)
*A61B 5/00* (2006.01)
(Continued)

(52) U.S. Cl.
CPC .......... *A61B 5/4875* (2013.01); *A61B 5/0205* (2013.01); *A61B 5/352* (2021.01);
(Continued)

(58) Field of Classification Search
CPC ..... A61B 5/4875; A61B 5/0205; A61B 5/352; A61B 5/021; A61B 5/02405; A61B 5/0816; A61B 5/02416; A61B 5/6898
(Continued)

(56) References Cited

U.S. PATENT DOCUMENTS 9,839,363 B2 * 12/2017 Albert .................. A61B 5/7267
10,674,939 B1 * 6/2020 Jones .................. A61B 5/7278
(Continued)

FOREIGN PATENT DOCUMENTS

WO    2016202442 A1    12/2016

OTHER PUBLICATIONS

Carter III, Robert et al., The influence of hydration status on heart rate variability after exercise heat stress; Journal of Thermal Biology (2005), vol. 30, pp. 495-502.
(Continued)

*Primary Examiner* — Tanmay K Shah
(74) *Attorney, Agent, or Firm* — Patterson Intellectual Property Law, P.C.; Jerry Turner Sewell

(57) ABSTRACT

A method for determining the hydration status of a person prompts the person to breathe while in a first postural position during which the method measures a first heart rate variability (HRV) value. The person is prompted to change to a second postural position, and the method measures a second HRV value. A difference between the first HRV value and the second HRV value is a daily score. The daily score is subtracted from a baseline to obtain a hydration score. In certain embodiments, the person is requested to respond to a plurality of subjective questions. The method processes the subjective responses and the daily score to determine whether the person is adequately hydrated. In certain embodiments of the method, the person is requested to identify the color of the person's urine. The identified color is processed with the daily score and the subjective responses to determine hydration.

16 Claims, 12 Drawing Sheets

(51) Int. Cl.
  *A61B 5/0205* (2006.01)
  *A61B 5/352* (2021.01)
  *A61B 5/08* (2006.01)
  *A61B 5/024* (2006.01)
  *A61B 5/021* (2006.01)
(52) U.S. Cl.
  CPC ........... *A61B 5/021* (2013.01); *A61B 5/02405* (2013.01); *A61B 5/0816* (2013.01)
(58) Field of Classification Search
  USPC .......................................................... 600/480
  See application file for complete search history.

(56) References Cited

U.S. PATENT DOCUMENTS

| | | | | |
|---|---|---|---|---|
| 2009/0043222 A1* | 2/2009 | Chetham | ................ | G16H 50/30 600/547 |
| 2015/0073723 A1* | 3/2015 | Mulligan | ............... | G16H 20/30 702/19 |
| 2015/0148623 A1* | 5/2015 | Benaron | .............. | A61B 5/7207 600/306 |
| 2015/0164349 A1* | 6/2015 | Gopalakrishnan | ... | A61B 5/0022 600/508 |

OTHER PUBLICATIONS

International Search Report and Written Opinion for corresponding PCT/US2020/034441, dated Sep. 18, 2020, 10 pages.

\* cited by examiner

PORTABLE DEHYDRATION MONITORING SYSTEM

CROSS-REFERENCE TO RELATED APPLICATION

This application claims the benefit under 35 U.S.C. § 119(e) of U.S. Provisional Patent Application No. 62/852,874, filed May 24, 2019, entitled "Portable Dehydration Monitoring System," which is hereby incorporated by reference in its entirety.

FIELD OF THE INVENTION

The present disclosure relates generally to a non-invasive system and a method for determining dehydration.

BACKGROUND

Maintenance of fluid and electrolyte balance is essential to healthy living and is particularly important in periods of ill health. Dehydration, overhydration, and salt and water overload have been associated with morbidity and mortality.

A state of dehydration occurs with excess loss of total body water and is often associated with electrolyte abnormalities, particularly changes in sodium concentration within the serum. Hypertonic (elevated sodium concentration) dehydration occurs when proportionally more water than sodium is lost from the extracellular fluid compartment. This may occur, for example, as a result of age-related thirst impairment, which is seen in older adults. Hypotonic (low sodium concentration) dehydration occurs when the proportion of sodium lost is greater than the proportion of water lost. This may occur, for example, with the use of diuretics or in burn victims. Isotonic dehydration results from proportionate loss of water and sodium, and results in normal serum sodium concentrations. This may occur, for example, as a result of diarrhea, where there is salt and water loss in equivalent proportions.

Heart rate and blood pressure may be affected by the state of hydration of the body. Heart rate and blood pressure are controlled by the autonomic nervous system. The autonomic nervous system itself comprises the sympathetic and parasympathetic nervous systems. The two systems may be considered as a paired system that is maintained in balance. Each system always provides some degree of nervous input to a given tissue. Because the sympathetic system and the parasympathetic system typically have opposing effects on a given tissue, increasing the activity of one system while simultaneously decreasing the activity of the other results in very rapid and precise control of a tissue's function.

When dehydration results in reduced volume in the intravascular compartment, the heart rate and blood pressure response is specifically controlled by the baroreceptor reflex. Baroreceptors are specialized pressure sensing neurons predominantly within the arch of the aorta, carotid sinuses and the heart. A change in blood pressure results in a change in stretch of the baroreceptors, which generates a signal that travels within the vagus nerve to the medulla oblongata of the brain. This signal is processed and results in a change in the balance of the sympathetic to parasympathetic activity. Generally, dehydration is expected to cause an increase in the ratio of sympathetic to parasympathetic activity. This results in the release of noradrenaline, constriction of peripheral blood vessels and an increase in the heart rate and stroke volume of the heart resulting in a maintained blood pressure.

Heart rate alone can be used as a marker of hydration as it will be significantly increased from baseline in the case of dehydration resulting from exercise or at rest. As an additional measure, hydration assessment using the cardiovascular response to standing has also been evaluated. The delta in heart rate between sitting and standing was correlated with increased water loss. As a standalone test (without comparing with baseline) an increase in heart rate of 20 beats per minute (bpm) was found to be a valid method of detecting dehydration, providing high specificity, but low sensitivity for 2-7% dehydration. Of note it was most accurate for hypertonic dehydration. Whilst heart rate increase from baseline has not been measured prospectively as a method of detecting dehydration, evidence suggests its utility as a vital sign for clinical assessment and that heart rate in the dehydrated state is significantly elevated from the hydrated state. Continuous or frequent monitoring coupled with contextual information to determine the patient's baseline state should be expected to provide a signal when a patient is significantly deviating from their baseline hydration levels.

Heart rate variability (HRV) is commonly used as a non-invasive easy-to-apply tool to determine the physiological status of an individual. HRV indicate variations in beat-to-beat intervals and autonomic nervous system activity. HRV can be analyzed by linear methods within the domains of time and frequency analyses. HRV can also be analyzed by nonlinear methods.

Because of the effect of dehydration on the autonomic nervous system (increasing sympathetic signals and reducing parasympathetic signals), dehydration would be expected to reduce heart rate variability. Reduction in HRV has been demonstrated in three clinical studies all of which have demonstrated a reduction in heart rate variability in the dehydrated state. Reduction in HRV has been shown in dehydration at rest as well as following exercise; and all changes were significant. These changes were also demonstrated over multiple methods for determining heart rate variability.

In a study of fourteen college athletes, HRV, urine specific gravity and body weight were measured at baseline. The athletes went through a dehydration protocol. Seven athletes (the rehydration group) were rehydrated subsequently. The other seven athletes (the dehydration group) remained dehydrated. The dehydration group demonstrated significant reduction in all measured parameters of dehydration while the rehydration group did not. See, M. Castro-Sepulveda, H. Cerda-Kohler, C. Pérez-Luco, M. Monsalves, D. C. Andrade, H. Zbinden-Foncea, et al., *Hydration status after exercise affect resting metabolic rate and heart rate variability*, Nutrición Hospitalaria (Nutr Hosp), 2014; 31(3): 1273-7.

In a second study, five subjects performed heat trials in the hydrated and dehydrated state (3.90-7% body weight loss). During each trial, cardiac cycle R-R interval data were collected for 45 minutes at rest before completing a 90-minute cycle ergometer exercise and were collected again for 45 minutes at rest after completing the exercise. An analysis was performed to measure the high-frequency (HF), low-frequency (LF), very low-frequency (VLF), and total power (TP) components of HRV. Overall HRV was significantly decreased by hypohydration. In this study, heart rate was also significantly increased in the dehydrated, resting state. See, R. Carter, S. Cheuvront, M. Kolka, L. Stephenson, and M. Sawka, *The influence of hydration status on heart rate variability after exercise heat stress*, Journal of Thermal Biology, 2005; 30(7):495-502.

In a third study, seventeen male athletes were assessed in three phases, before any physical activity, post-exercise (after pedaling a stationary bike), and post-rehydration (after the subjects drank water ad libitum). See. E. Severeyn, J. Velásquez, G. Perpiñán, H. Herrera, M. Pachec, and S. Wong, *Heart rate variability analysis during a dehydration protocol on athletes*, 2016 XXI Symposium on Signal Processing, Images and Artificial Vision (STSIVA), 2016. An electrocardiographic acquisition and a weight measure were performed in each phase. The study of HRV in each of the electrocardiographic signals was performed by obtaining time-domain parameters (RR, RMSSD, SDRR), frequency-domain parameters (LF, HF) and non-linear parameters (SD1, SD2, approximate entropy and scaled exponents: $\alpha1$ and $\alpha2$), as described, for example, in J. Sztajzel, *Heart rate variability: a noninvasive electrocardiographic method to measure the autonomic nervous system*, Swiss Med Wkly. 2004; 134(35-36):514-22. The findings in this paper imply that parameters: RR, RMSSD, SDRR, LF, HF, $\alpha2$, SD1 and SD2 from HRV, were able to differentiate between phases of hydration and dehydration in the individual athlete.

Moving from a seated to a standing position instigates a change in blood pressure which in turn causes a change in the stretch of baroreceptors. This leads to a change in the balance of the sympathetic to parasympathetic activity. Dehydration is expected to lead to an increased change from sympathetic to parasympathetic activity. See, for example, M. Castro-Sepulveda, et al., cited above. The degree of this change can be measured through HRV features.

HRV may be determined through the method of photoplethysmography (PPG) using a smartphone application. One such application is commercially available from Autonom Health Gesundheitsbildungs GmbH of Vienna, Austria. A PPG measurement is obtained by a user holding his or her index finger over the lens of the smartphone camera with the accompanying camera LED (flashlight) switched on. A PPG signal is obtained by measuring the subsequent reflection of light while the user's finger is illuminated and is covering the smartphone camera. See, for example, D. J. Plews, B. Scott, M. Altini, M. Wood, A. E. Kilding, P. B. Laursen, *Comparison of Heart-Rate-Variability Recording With Smartphone Photoplethysmography, Polar H7 Chest Strap, and Electrocardiography*, Int J Sports Physiol Perform, 2017; 12(10):1324-8, which is incorporated herein by reference.

SUMMARY

The HRV measurement application system and method disclosed herein are intended to be used in conjunction with a postural change test (sit-stand test) to monitor whether a patient is in a state of hydration or dehydration. The system and method operate by tracking changes in specific HRV features during the postural change. The system and method use a smartphone camera photoplethysmography acquisition application such as, for example, the application from Autonom Health Gesundheitsbildungs GmbH of Vienna, Austria, identified above. The system and method are configured to be used daily in both in-patient and out-patient settings to provide information to patients and to medical professionals. The data provided by the system and method enable patient self-management of hydration status. The system and method are also able to alert a clinical team to changes in the patient condition that may warrant specific intervention.

In order to determine if a user is dehydrated the system and method disclosed herein direct a user to perform the steps of a seated to standing test. First, the patient remains seated and follows an on-screen breathing guide for ten to thirty seconds. The system and method obtain an HRV reading during the test. At the end of the ten- to thirty-second seated test, the user is directed to stand up immediately. The system and method repeat the HRV reading when the user stands.

The system and method use the HRV readings from the sitting test and the standing test to determine a "hydration score" by calculating the difference between the user's HRV readings. The difference is calculated as an absolute change such that the difference is always non-negative number.

At the conclusion of the two steps of the test, the system and method ask the user a series of clinically proven subjective questions. The questions include, but are not limited to, whether the user is experiencing any sensations of thirst, lightheadedness upon standing, nausea, or reduced oral intake. The user is asked to describe an estimated color of his or her urine. Each response from the user is assigned a weighted score.

The system and method apply an algorithm to the test results and to the weighted responses from the user to determine if a patient is in a state of hydration or dehydration. The results of the algorithm are represented by a flag (symbol) having a selected color (e.g., green, yellow, or red). The flag is displayed to the user at the completion of each test. A green flag means the user is in a state of hydration. A yellow flag means the user is in a state of mild dehydration or is at risk of severe dehydration. A red flag means the user is in a state of severe dehydration or is at a very high risk of being in a state of severe dehydration.

The dehydration algorithm performed by the system and method works best when a user's baseline hydration reading is determined. The baseline hydration reading is determined by taking the rolling average of a plurality of "good" readings from the user (e.g. seven or thirty days). A "good" reading is a reading in which a user is screened via health questions to determine if the user is likely to be in a state of dehydration. By taking a weighted average, the algorithm can determine whether the user's hydration status is stable and is therefore representative of the user being in his or her "baseline hydrated state."

This method of measuring a baseline for a patient's hydrated state is effective because, no matter what state a user is in, if the user's "hydration score" (the change between the seated HRV readings and the standing HRV readings) increases, then the patient is under more stress when standing and is therefore dehydrated. An accurate baseline enables the algorithm to determine to what degree a patient is dehydrated.

Over time, as more data is collected from many users, a baseline score for each user will no longer be needed to understand to what degree of dehydration a user is in. Over time, the data set will become sufficiently large to determine the patterns in changes of HRV among different patient populations in different states of dehydration.

The system and method for acquiring the PPG reading may change from acquisition via a smartphone camera, to acquisition of HR data directly through an electrocardiograph (ECG) embedded inside a stoma bag or a base plate. Additionally or alternatively, a remote ECG sensor may be implemented separate from a stoma bag or a base plate, such as a remote ECG sensor on a wearer's body which may be wirelessly coupleable to an application or an electronic device configured to receive at least one ECG signal from the ECG sensor. At least one ECG sensor may be implemented by a wearable tracking device, such as a BIO- STRAP®, an APPLE WATCH®, a FITBIT®, or other wearable electronic device capable of measuring an ECG value and/or a value useable to determine an ECG reading value. Moreover, the changes in acquisition method can be coupled with the automatic detection of postural change using accelerometers, a gyroscope, or both, so that the system and method can take a reading without any explicit interaction from the user. Additionally or alternatively, at least one PPG reading may be measured by or in conjunction with a wearable tracking device, such as a BIOSTRAP®, an APPLE WATCH®, a FITBIT®, or other wearable electronic device capable of measuring a value useable to determine a PPG reading value, either in whole or in part. The additional features allow continuous monitoring of a user's hydration status.

One aspect in according to the embodiments disclosed herein is method for determining the hydration status of a person. The method prompts the person to breathe while in a first postural position during which the method measures a first heart rate variability (HRV) value. The person is prompted to change to a second postural position, and the method measures a second HRV value. A difference between the first HRV value and the second HRV value is a daily score. A baseline value is calculated for the person according to historical HRV data and storing the baseline value at the electronic device. The daily score is subtracted from a baseline to obtain a hydration score. In certain embodiments, the person is requested to respond to a plurality of subjective questions. The method processes the subjective responses and the daily score to determine whether the person is adequately hydrated. In certain embodiments of the method, the person is requested to identify the color of the person's urine. The identified color is processed with the daily score and the subjective responses to determine hydration.

Another aspect in accordance with the embodiments disclosed herein is a method for determining the hydration status of a person. The method obtains at least one photoplethysmography (PPG) reading from the person using a camera and associated lighting source of an electronic device. The method prompts the person to breathe at a first selected pace for a first selected duration while in a first postural position. The method measures the person's heart rate variability (HRV) during the first selected duration to obtain a first HRV value. The method prompts the person to change from the first postural position to a second postural position. The method prompts the person to breathe at a second selected pace for a second selected duration while in the second postural position. The method measures the person's HRV during the second selected duration to obtain a second HRV value. The method calculates a difference between the first HRV value and the second HRV value to generate a daily score. The method calculates a baseline value for the person according to historical HRV data and storing the baseline value at the electronic device. The method subtracts a baseline value from the daily score to obtain a hydration score.

In certain embodiments in accordance with this aspect, the first postural position is the user seated; and the second postural position is the user standing.

In certain embodiments in accordance with this aspect, the first postural position is the user in a supine position; and the second postural position is the user standing.

In certain embodiments in accordance with this aspect, the method requests the person to respond to a plurality of subjective questions to produce a corresponding plurality of subjective responses. The method processes the plurality of subjective responses and the daily score to determine whether the person is adequately hydrated.

In certain embodiments in accordance with this aspect, the first time duration is between 10 and 30 seconds; and the second time duration is approximately the same as the first time duration.

In certain embodiments in accordance with this aspect, the plurality of subjective questions comprises:
  asking whether the person is experiencing excessive thirst to cause the person to input a first response;
  asking whether the person felt light-headed upon changing from the first postural position to the second postural position to cause the person to input a second response; and
  asking whether the person is experiencing nausea, vomiting or reduced oral intake to cause the person to input a third response.

In certain embodiments in accordance with this aspect, the method comprises generating a first response value when the first response is satisfies a dehydration threshold; generating a second response value when the second response is YES; generating a third response value when the third response is YES.

In certain embodiments in accordance with this aspect, the method applies a first weighting factor to the first response value; applies a second weighting factor to the second response value; and applies a third weighting factor to the third response value.

In certain embodiments in accordance with this aspect, the method asks the person to identify the color of the person's urine by selecting one of clear, pale, light yellow, dark yellow or brown. The method determines the person's hydration state based on the first response, the second response, the third response, and the identified color of the person's urine.

In certain embodiments in accordance with this aspect, the baseline value is determined by directing the person to perform a plurality of tests. Within each test, the method comprises obtaining at least one photoplethysmography (PPG) reading from the person using a camera and associated lighting source of an electronic device. The method includes prompting the person to breathe at a first selected pace for a first selected duration while in the first postural position. The method measures measuring the person's heart rate variability (HRV) during the first selected duration to obtain the first HRV value. The method further comprises prompting the person to change from the first postural position to the second postural position. The method prompts the person to breathe at a second selected pace for a second selected duration while in the second postural position. The method measures the person's HRV during the second selected duration to obtain the second HRV value. The method calculates a difference between the first HRV value and the second value to generate an HRV difference value. The method determines whether the HRV difference value is greater than a maximum value. If the HRV difference value is greater the maximum value, the method prompts the person to hydrate and to retake the test later. If the HRV difference value is not greater than the difference value, the method requests the person to respond to a plurality of subjective questions to produce a corresponding plurality of subjective responses. The method processes the plurality of subjective responses to determine whether to save the HRV difference value or to prompt the user to retake the test later. The method averages the saved HRV difference values to generate the baseline value.

In certain embodiments in accordance with this aspect, the method determines whether to save the HRV difference value by counting a number of YES responses. In certain embodiments in accordance with this aspect, the subjective questions comprise:

asking whether the person is experiencing excessive thirst to cause the person to input a first response;

asking whether the person felt light-headed upon changing from the first postural position to the second postural position to cause the person to input a second response; and asking whether the person is experiencing nausea, vomiting or reduced oral intake to cause the person to input a third response.

In certain embodiments in accordance with this aspect, the plurality of tests comprises a plurality of tests in which the HRV difference value is saved.

In certain embodiments in accordance with this aspect, the method further comprises asking the person to identify the color of the person's urine by selecting one of clear, pale, light yellow, dark yellow or brown; and determining the person's hydration state based on the plurality of subjective responses and the identified color of the person's urine.

A method for determining the hydration status of a person obtains at least one photoplethysmography (PPG) reading from the person using a camera and associated lighting source of an electronic device. The method prompts the person to breathe at a first selected pace for a first selected duration while the person is in a seated position. The method measures the person's heart rate variability (HRV) during the first selected duration to obtain a first HRV value. The method prompts the person to rise to a standing position. The method prompts the person to breathe at a second selected pace for a second selected duration while the person is in the standing position. The method measures the person's HRV during the second selected duration to obtain a second HRV value. The method calculates a difference between the first HRV value and the second HRV value to generate a daily score. The method calculates a baseline value for the person according to historical HRV data and storing the baseline value at the electronic device. The method subtracts a baseline value from the daily score to obtain a hydration score.

A method for determining a hydration status of a person may include obtaining at least one of a photoplethysmography (PPG) measurement value or an electrocardiogram (ECG) measurement value from the person. The method may transmit the obtained at least one PPG measurement value or ECG measurement value to an electronic device. The person may be prompted to breathe at a first selected pace for a first selected duration while in a first postural position. The person's heart rate variability (HRV) may be measured during the first selected duration to obtain a first HRV value, after which the person may be prompted to change from the first postural position to a second postural position. The person may be prompted to breathe at a second selected pace for a second selected duration while in the second postural position, and the person's HRV may be measured during the second selected duration to obtain a second HRV value. A difference between the first HRV value and the second HRV value may be calculated to generate a daily score. A hydration score may be determined based at least in part upon the daily score and one or more sets of hydration status information may be stored at the electronic device.

BRIEF DESCRIPTIONS OF THE SEVERAL VIEWS OF THE DRAWINGS

The foregoing aspects and other aspects of the disclosure are described in detail below in connection with the accompanying drawings in which.

Figure 6A:
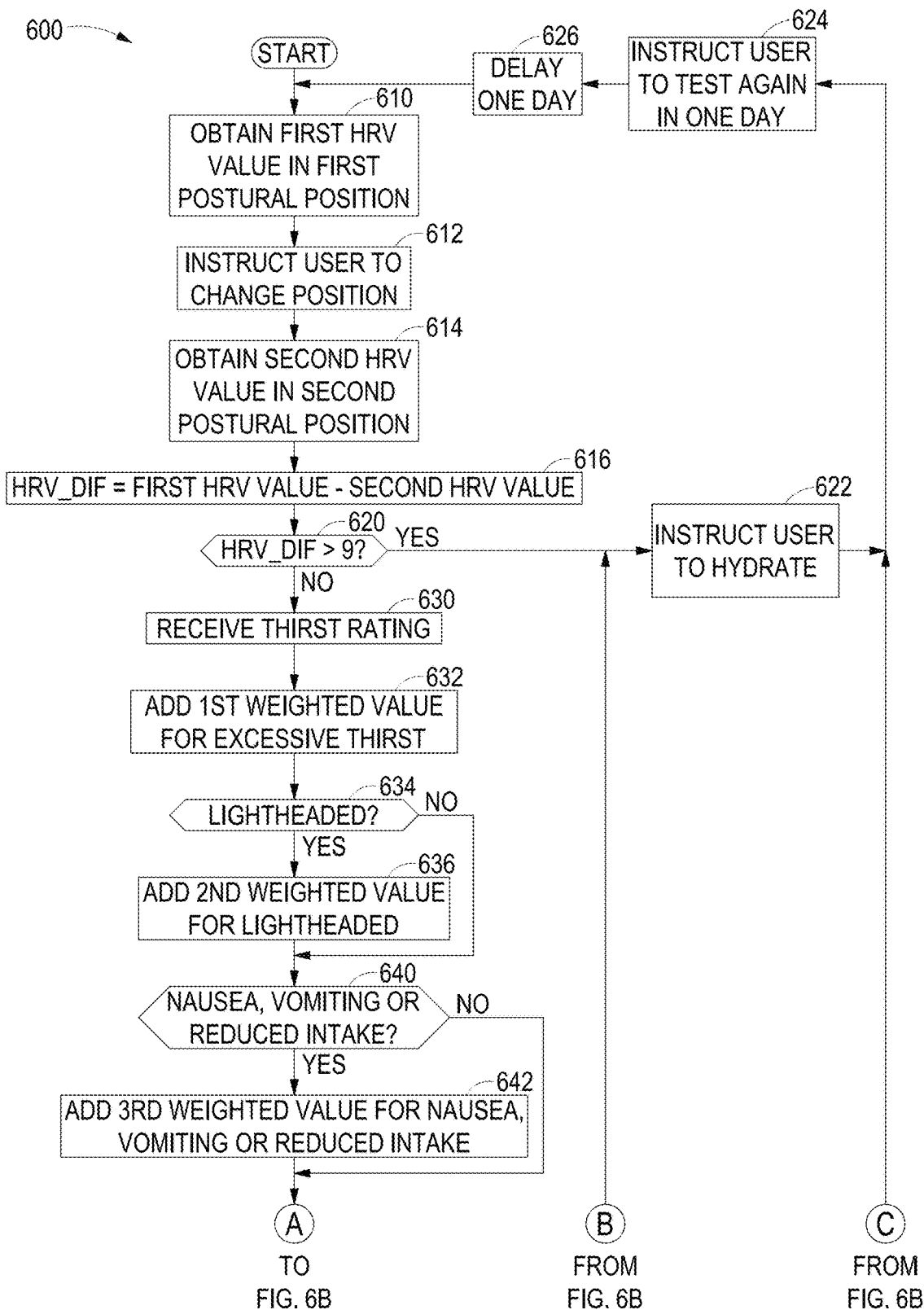
Figure 6B:
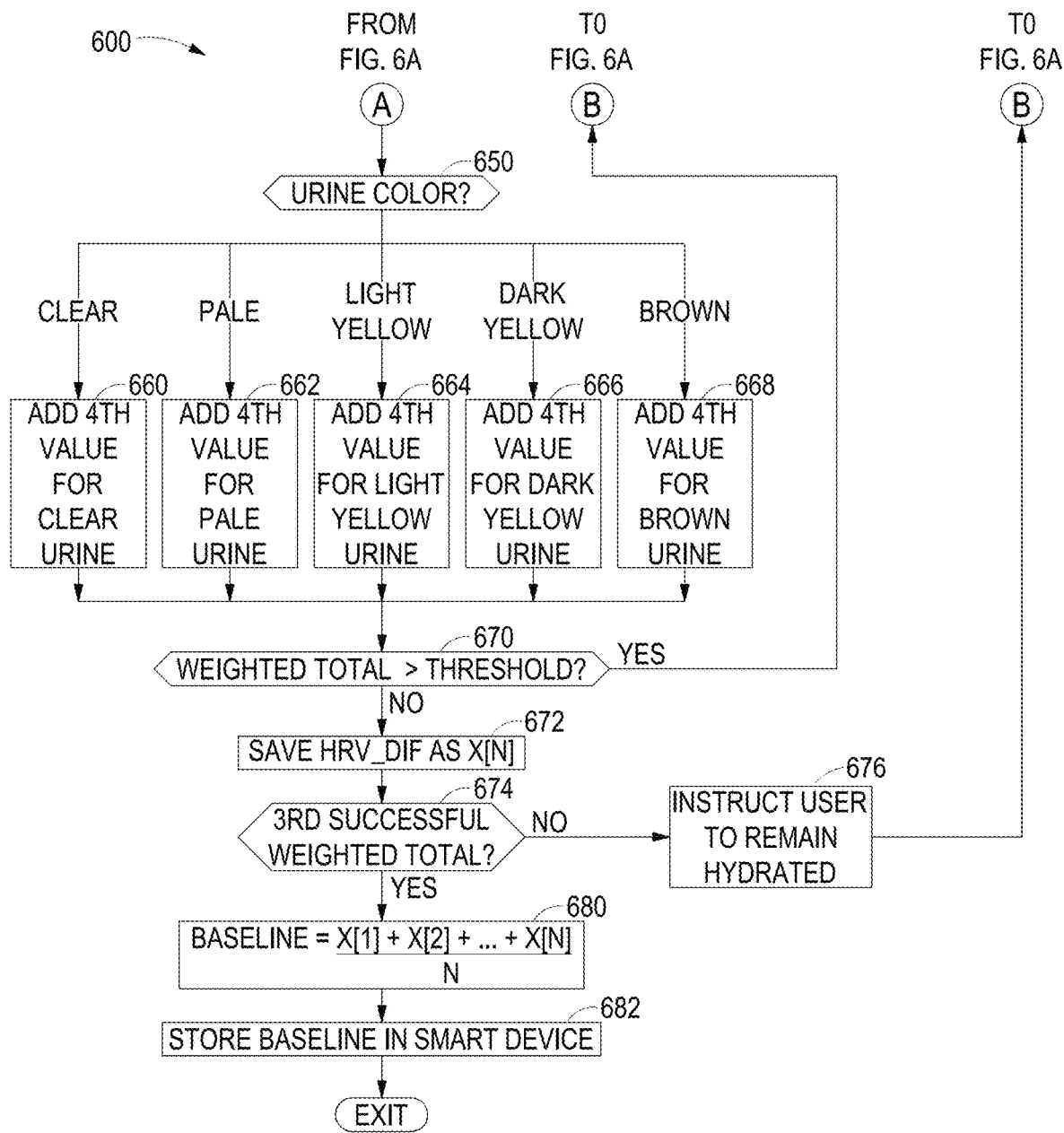
Figure 7A:
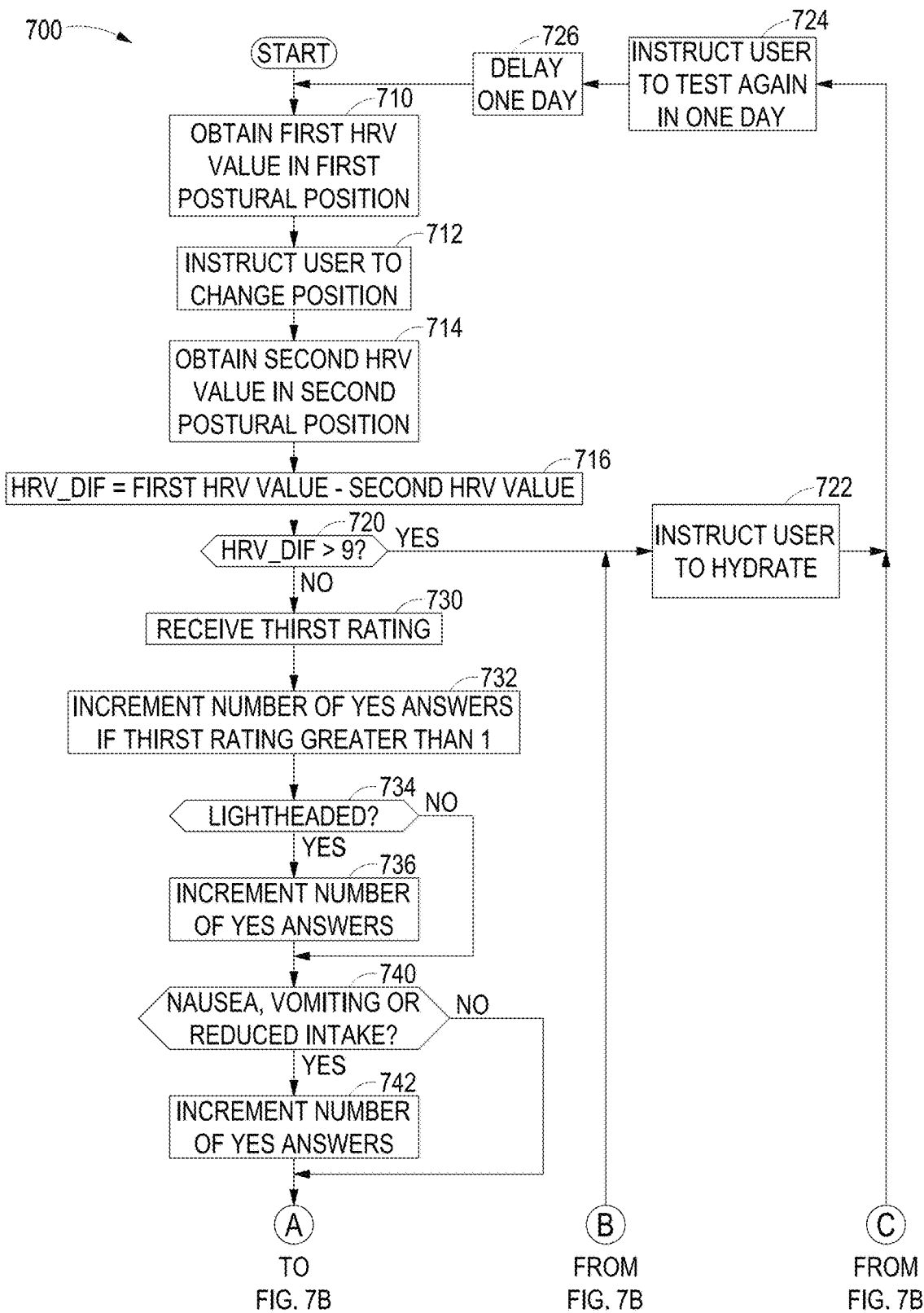
Figure 7B:
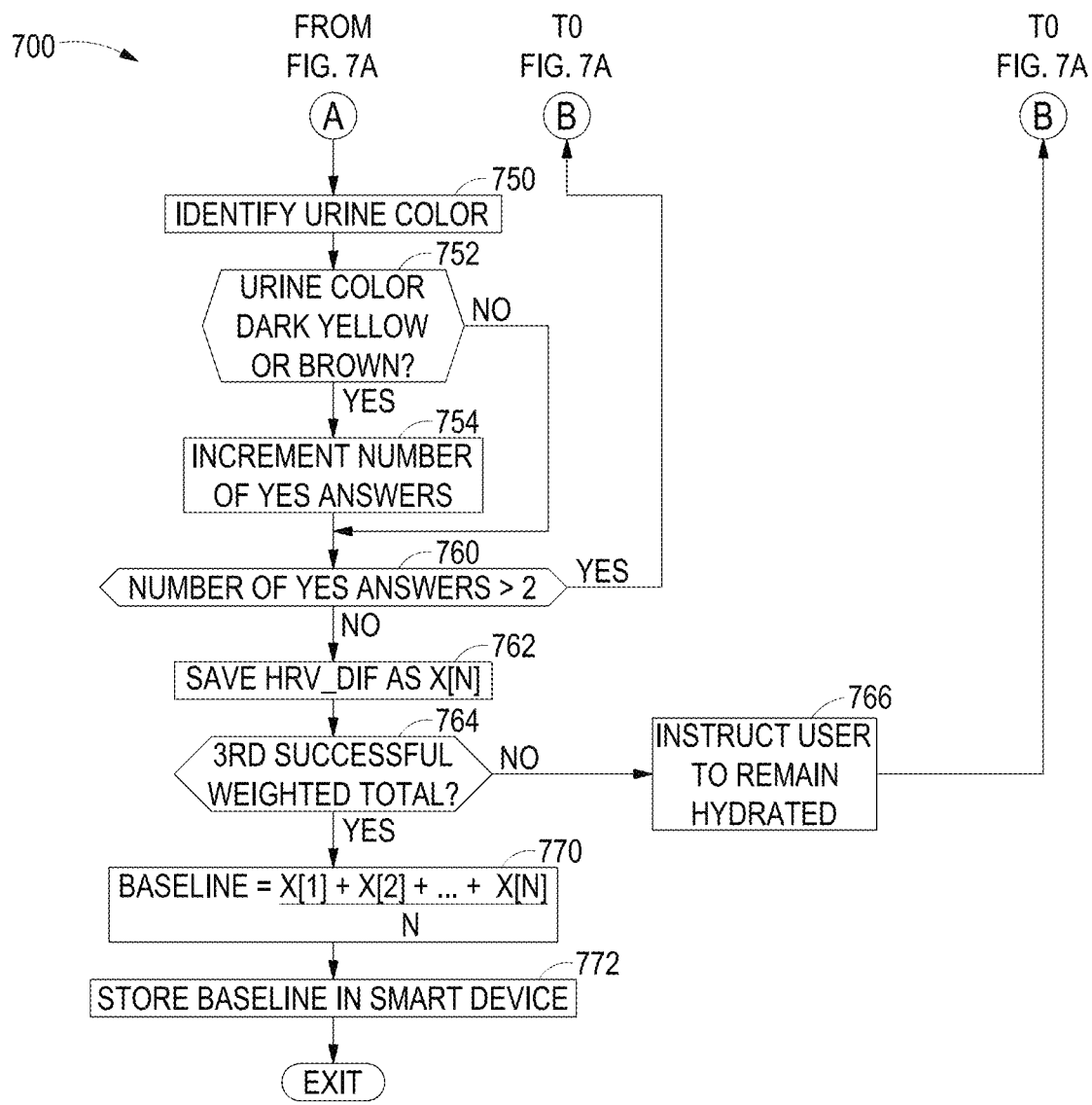
Figure 8A:
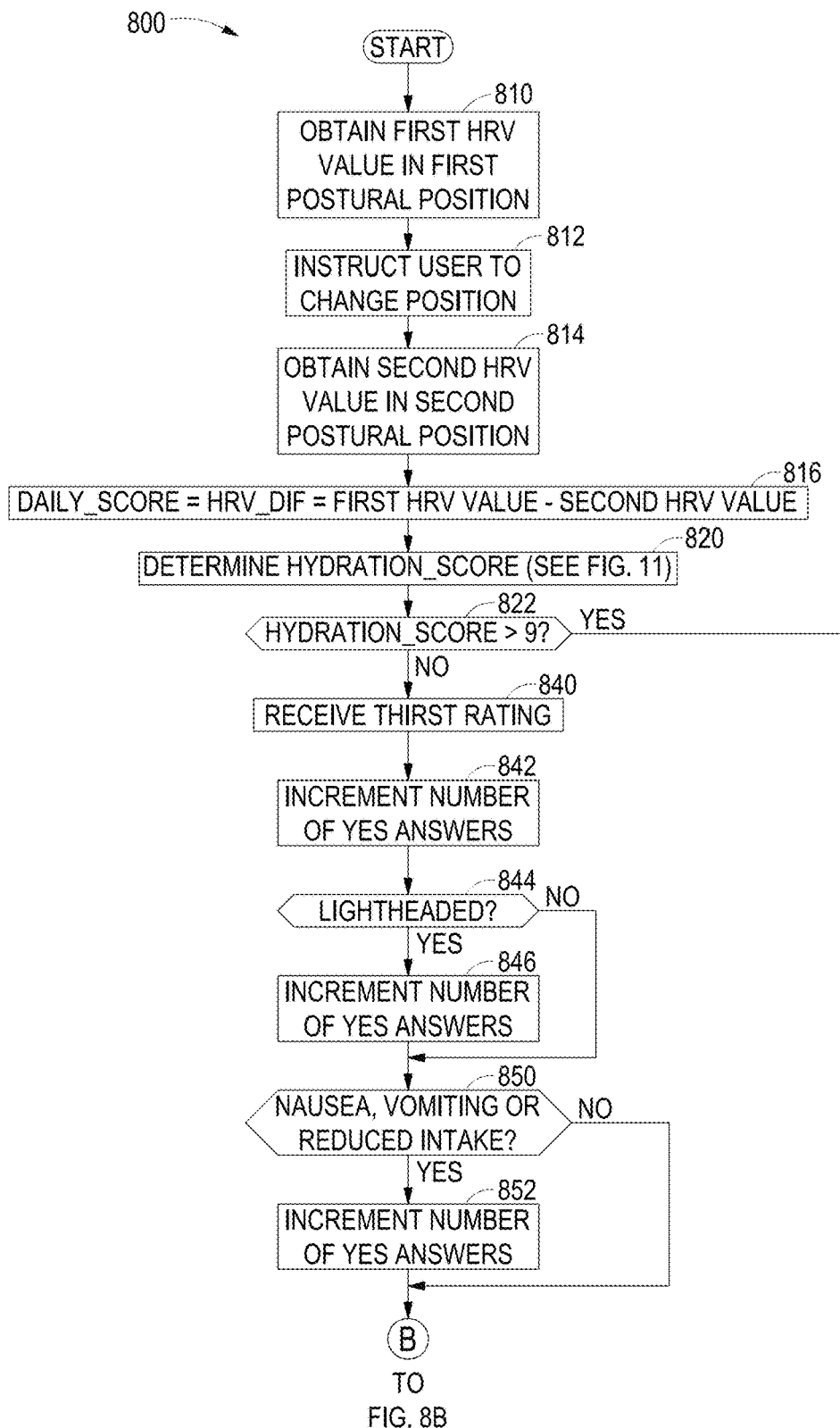
Figure 8B:
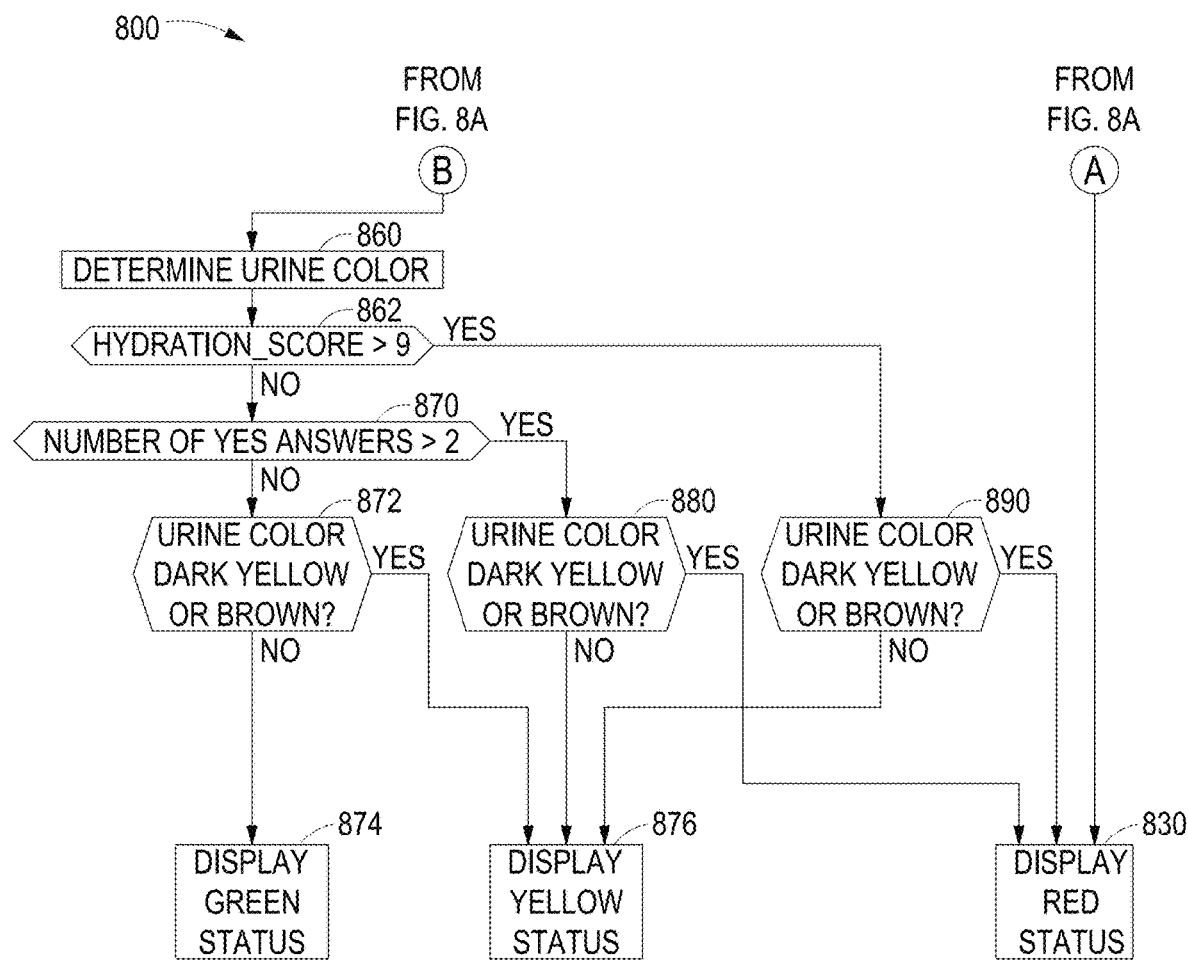
Figure 9:
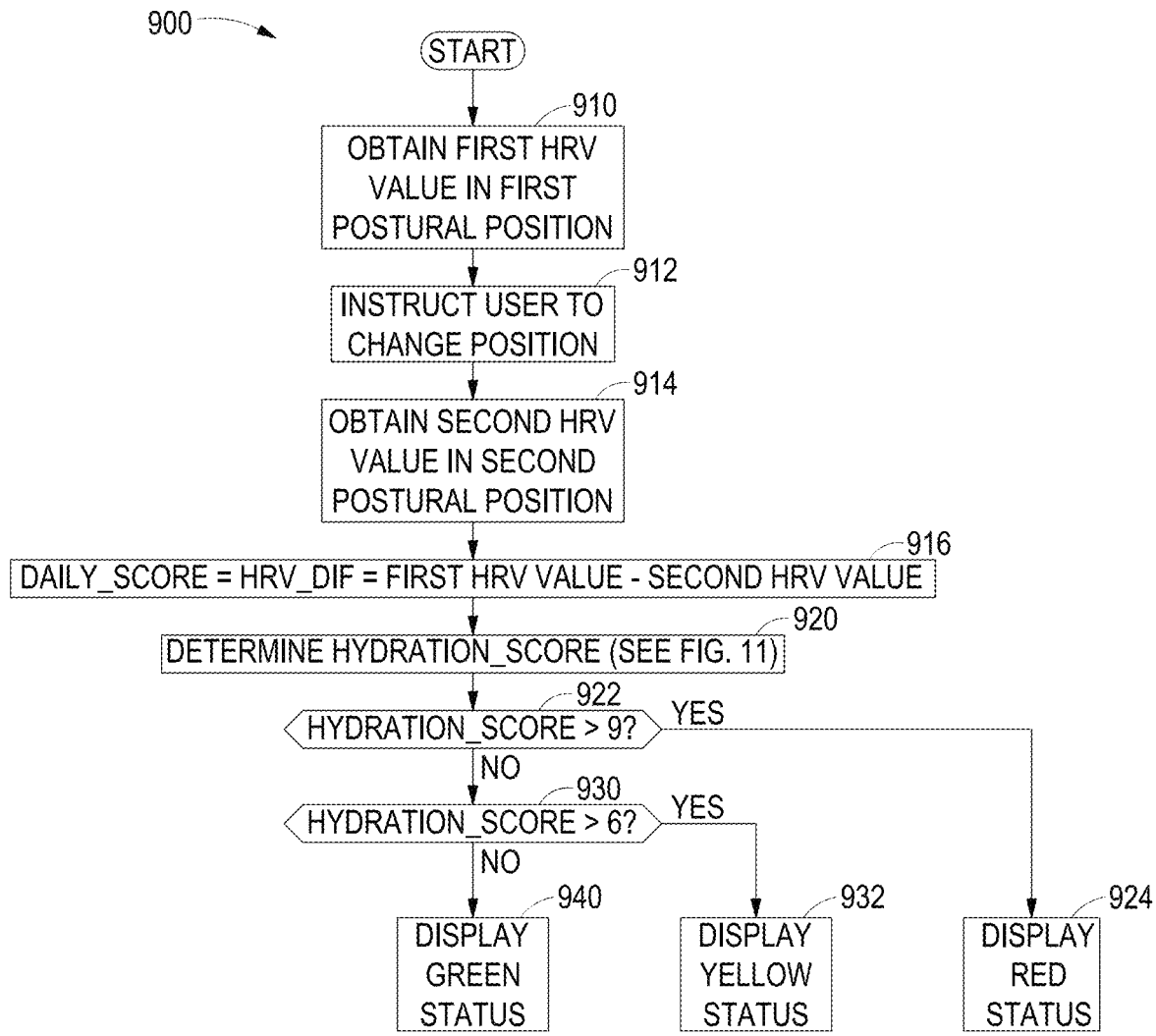

FIG. 6A and FIG. 6B together illustrate a flowchart representing a first embodiment of a method for determining a baseline heart rate variability (HRV) difference caused by a transition from a first postural position to a second postural position;

FIG. 7A and FIG. 7B together illustrate a flowchart representing a second embodiment of a method for determining a baseline heart rate variability (HRV) difference caused by a transition from a first postural position to a second postural position;

FIG. 8A and FIG. 8B together illustrate a flowchart representing an embodiment of a method for determining a hydration score based on a difference between a current heart rate variability difference caused by a transition from a first postural position to a second postural position and a baseline heart rate variability difference determined in accordance with the method of FIGS. 6A and 6B or in accordance with the method of FIGS. 7A and 7B; and FIG. 9 illustrates a flowchart representing an embodiment of a method for determining a hydration score based on a difference between a current heart rate variability difference caused by a transition from a first postural position to a second postural position and a baseline heart rate variability difference wherein the determination of hydration is obtained without prompting the user to respond to subjective questions.

Figure 10:
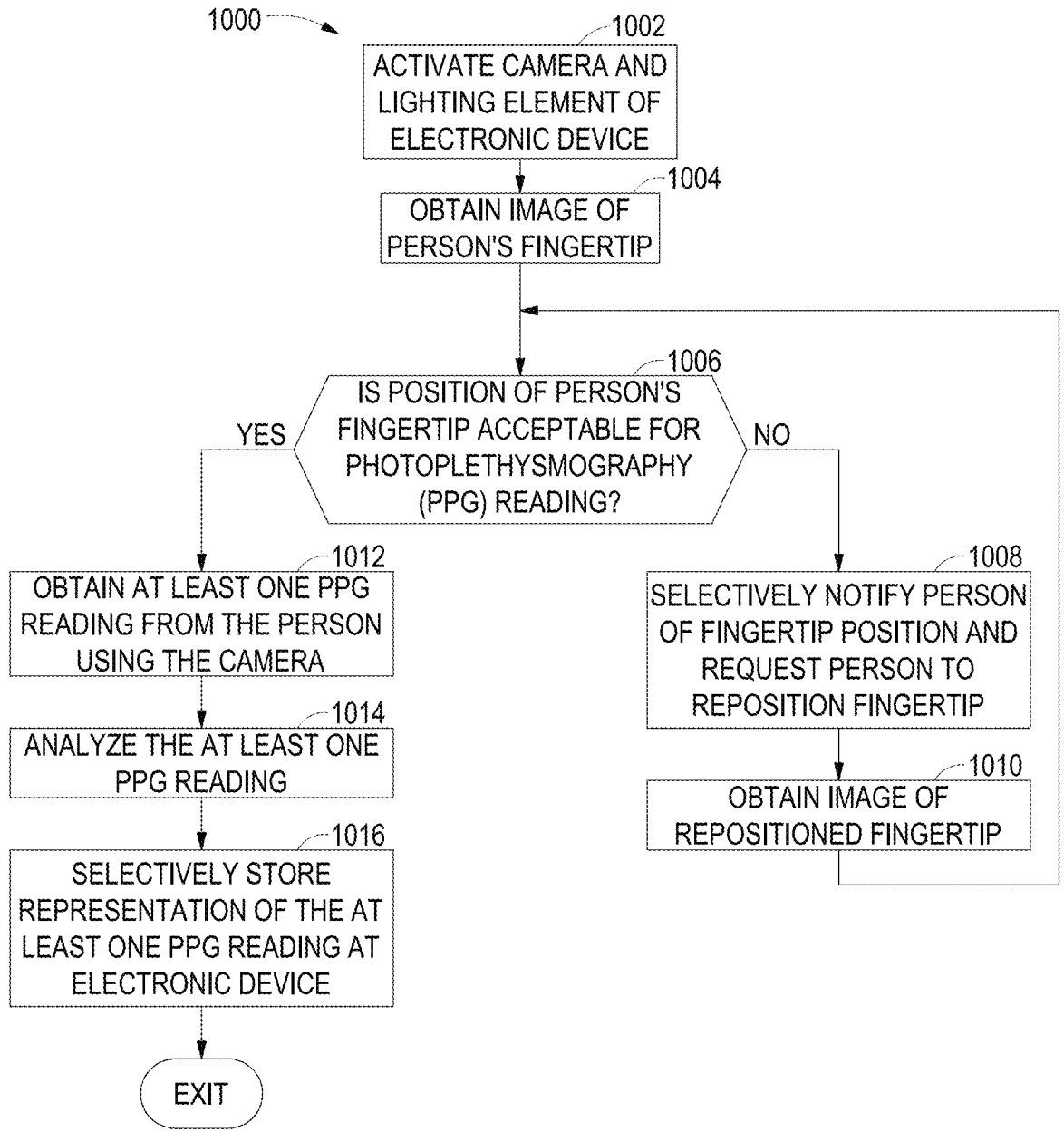

FIG. 10 illustrates an exemplary embodiment of a process for positioning a person's finger for use with a photoplethysmography (PPG) measurement device according to aspects of the present disclosure.

Figure 11:
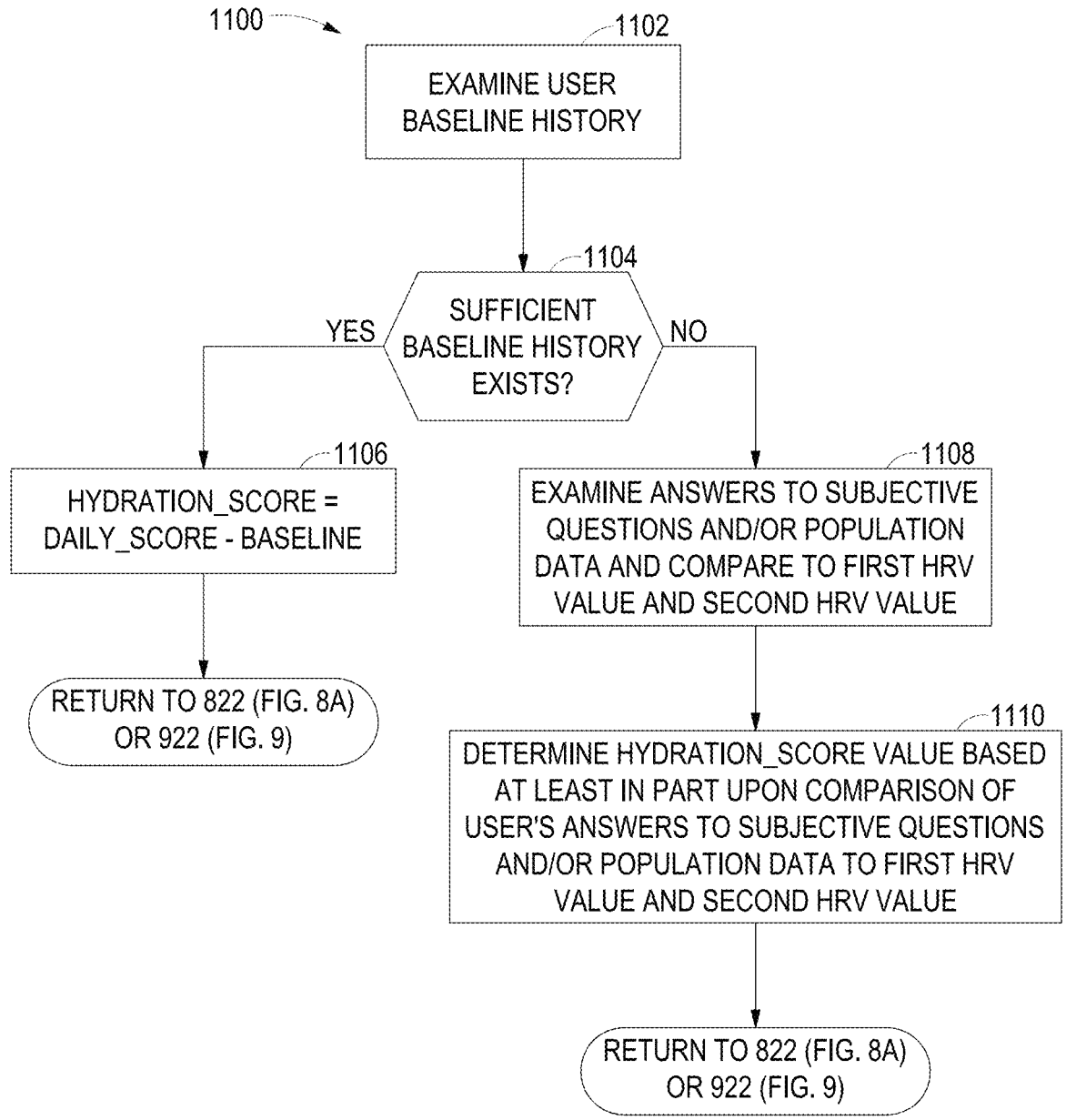

FIG. 11 illustrates an exemplary embodiment of a process for determining a hydration score for a user according to aspects of the present disclosure.

DETAILED DESCRIPTION

The following detailed description of embodiments of the present disclosure refers to one or more drawings. Each drawing is provided by way of explanation of the present disclosure and is not a limitation. Those skilled in the art will understand that various modifications and variations can be made to the teachings of the present disclosure without departing from the scope of the disclosure. For instance, features illustrated or described as part of one embodiment can be used with another embodiment to yield a still further embodiment.

The present disclosure is intended to cover such modifications and variations as come within the scope of the appended claims and their equivalents. Other objects, features, and aspects of the present disclosure are disclosed in the following detailed description. One of ordinary skill in the art will understand that the present discussion is a description of exemplary embodiments only and is not intended as limiting the broader aspects of the present disclosure.

Figure 1A:
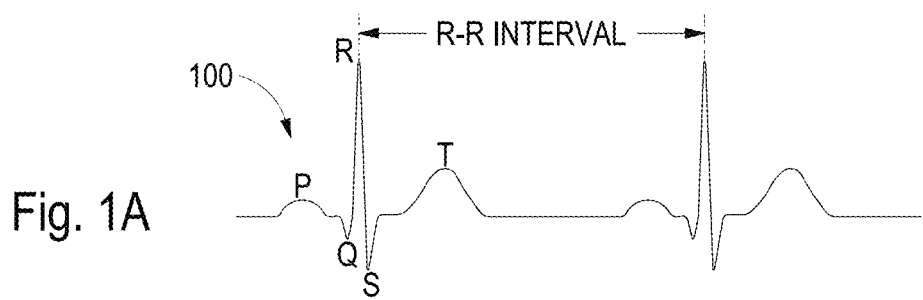
FIG. 1A illustrates an example of an electrocardiograph (ECG) waveform.
Figure 1B:
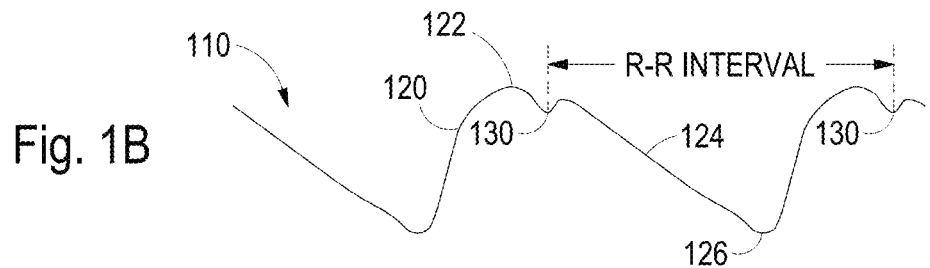
FIG. 1B illustrates an example of a photoplethysmographic (PPG) waveform.

FIG. 1A illustrates an example of an electrocardiograph (ECG) waveform 100 and FIG. 1B illustrates a photoplethysmographic (PPG) waveform 110. The ECG waveform represents the electrical signals within the heart and is obtained using an electrocardiogram device having a plurality of electrodes attached to the body of a subject. The PPG waveform represents the blood pressure of a subject taken at a peripheral location of the body of the subject. For example, the PPG waveform may be obtained by applying a PPG measurement device to a finger of the subject.

As illustrated by the ECG waveform 100 in FIG. 1A, each heartbeat is represented by a plurality of known features (e.g., waves) on the ECG waveform designated as P, Q, R, S and T. The R wave is the largest wave and provides a measurement landmark for analyzing the ECG waveform. As annotated on the ECG waveform, the distance between successive R waves represents an RR-interval, which corresponds to the time between successive heartbeats. The heart rate (HR) is determined as 1/(RR-interval).

With modern technology, the heart rate can be measured in a simpler manner by measuring the blood pressure using the PPG waveform 110. As shown in FIG. 1 B, the PPG waveform tracks the ECG waveform 100. For example, each R wave in the ECG waveform is followed in time by a rising systolic pulse 120 in the PPG waveform which increases to a maximum magnitude at a systolic peak 122. The PPG waveform then decreases along a diastolic wave 124 towards a minimum magnitude at a diastolic trough 126. As further shown in FIG. 1B, the PPG waveform includes a dicrotic notch 130 in the diastolic wave. The dicrotic notch represents a slight increase in the arterial pressure when the aortic valve closes, after which the diastolic wave continues to decrease to the diastolic trough.

As shown in FIG. 1 B, the PPG waveform 110 is synchronized with the ECG waveform 110 such that corresponding features in successive systolic-diastolic waves in the PPG waveform are spaced apart by the same RR-interval by which the R waves are spaced apart in the ECG waveform. Accordingly, the period of the heartbeat (HR) can be readily determined by measuring the time between successive repeated features of the PPG waveform. The location of the dicrotic notch is generally well-defined on the PPG waveform. Thus, the period (RR-interval) of the heartbeat is often measured between successive dicrotic notches as shown in FIG. 1B.

The heart rate (HR) of a person is not constant. Rather, the RR-interval between successive heartbeats may vary from beat to beat. The fluctuation of the RR-intervals between adjacent heartbeats is referred to as heart rate variability (HRV). HRV is generated by heart-brain interactions and by dynamic non-linear autonomic nervous system (ANS) processes. HRV helps a person adapt to environmental and psychological challenges. HRV reflects regulation of autonomic balance, blood pressure, gas exchange, gut, heart, and vascular tone. Vascular tone refers to the diameters of the blood vessels that regulate blood pressure.

The fluctuations in the heart rate of a healthy heart are complex and non-linear and may be described as mathematical chaos. The variability of the heart rate in a healthy person provides the flexibility of the person to rapidly cope with an uncertain and changing environment. Certain diseases of the body may result in either a loss of complexity or an increase in complexity in the HRV HRV is affected by a person's heart rate. When a person's heart beats faster, the time interval (RR-interval) between adjacent heartbeats is shorter. The faster heart rate results in less time for variations in the RR-interval. Accordingly, the HRV for a health heart is generally lower at greater heart rates.

The heart rate and HRV are affected by the state of hydration of a person's body. The effect of the state of hydration on HRV is evidenced, for example, by changes in HRV when a person's posture changes rapidly (e.g., from a sitting position to a standing position). When a properly hydrated person stands, the heart rate will increase, and the HRV may also change by a relatively small amount. In contrast, if the same person is in a dehydrated state, the lower volume of blood will cause the heart rate to increase as before; however, the HRV decreases significantly as the heart pumps harder and more rhythmically to maintain blood pressure after the postural change.

The system and method disclosed herein determines the differences in HRV between a person in a first postural position (e.g., a sitting position) and the same person immediately after transitioning to a second postural position (e.g., a standing position). The system and method compare the current differences in the HRV to previously determined baseline differences in HRV for the same person in a known properly hydrated condition to determine whether the person is dehydrated. The complete test is performed in less than two minutes and is sufficiently accurate to enable the person to take steps (e.g., consume liquids) if potential or actual dehydration is present.

Figure 2:
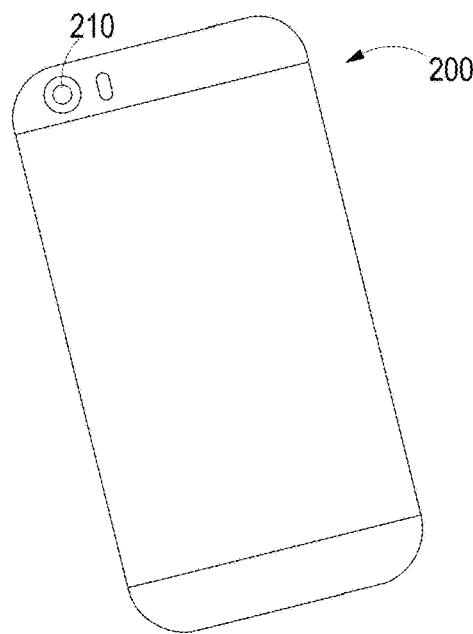
FIG. 2 illustrates a rear (distal) view of a smartphone showing the camera lens located thereon.
Figure 3:
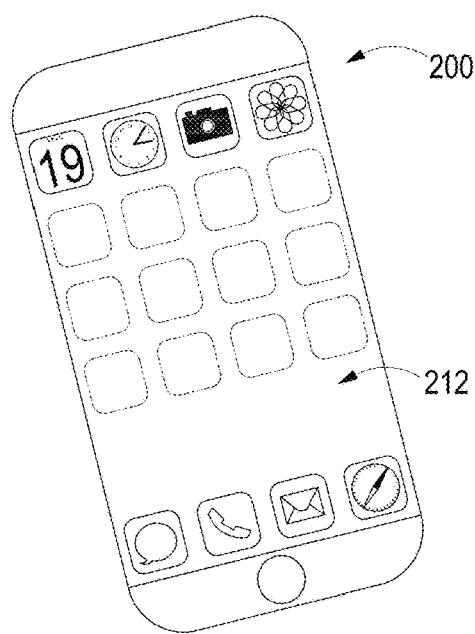
FIG. 3 illustrates a front (proximal) view of the smartphone of FIG. 2.
Figure 4:
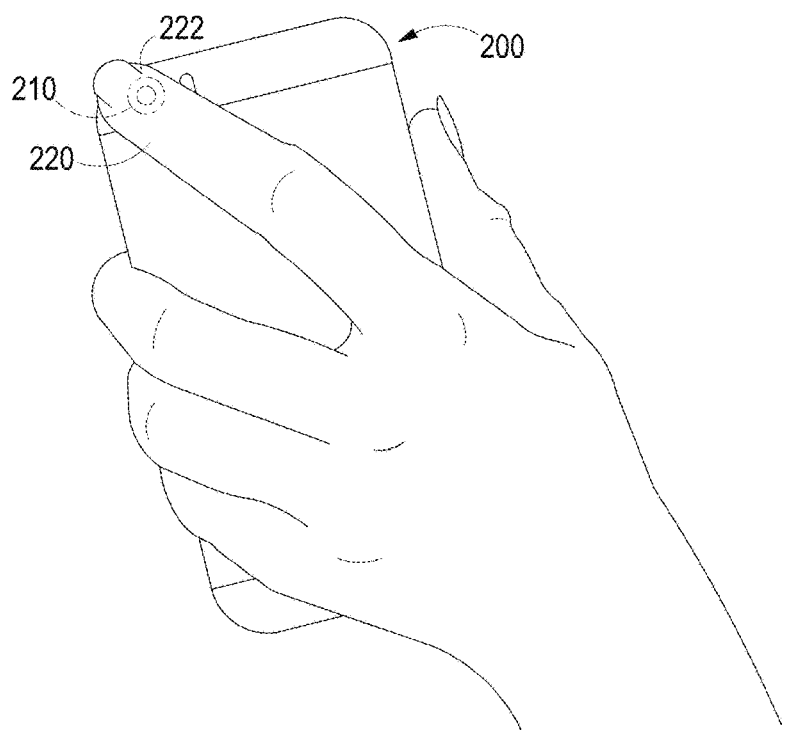
FIG. 4 illustrates the rear view of the smartphone in FIG. 2 with the fingertip of the left index finger of user placed over the camera lens of the smartphone.

FIG. 2 illustrates the distal (rear) surface of a smartphone 200 that implements the system and method disclosed herein. As shown in FIG. 2, the distal surface of the smartphone includes a camera lens 210. The smartphone includes a display screen 212 on the front side of the smartphone as shown in FIG. 3. The user grips the smartphone as shown in FIG. 4 such that the tip 222 of the user's index finger 220 is over the camera lens. The smartphone is then rotated as shown in FIG. 4 so that the user can visually monitor the instructions provided by the system and method while maintain the tip of the index finger over the camera lens. The instructions may also be provided verbally or by a combination of visual and verbal instructions.

When the user initiates the system and method, the system and method turn on the light-emitting diode (LED) light source (not shown) associated with the camera lens 210 of the smartphone 200 to cause light to be directed onto the user's fingertip and to be reflected into the camera lens. The use of a smartphone camera and light source to obtain PPG readings is described, for example, in D. J. Plews, et al., which was cited above, and which is incorporated herein by reference.

Figure 5:
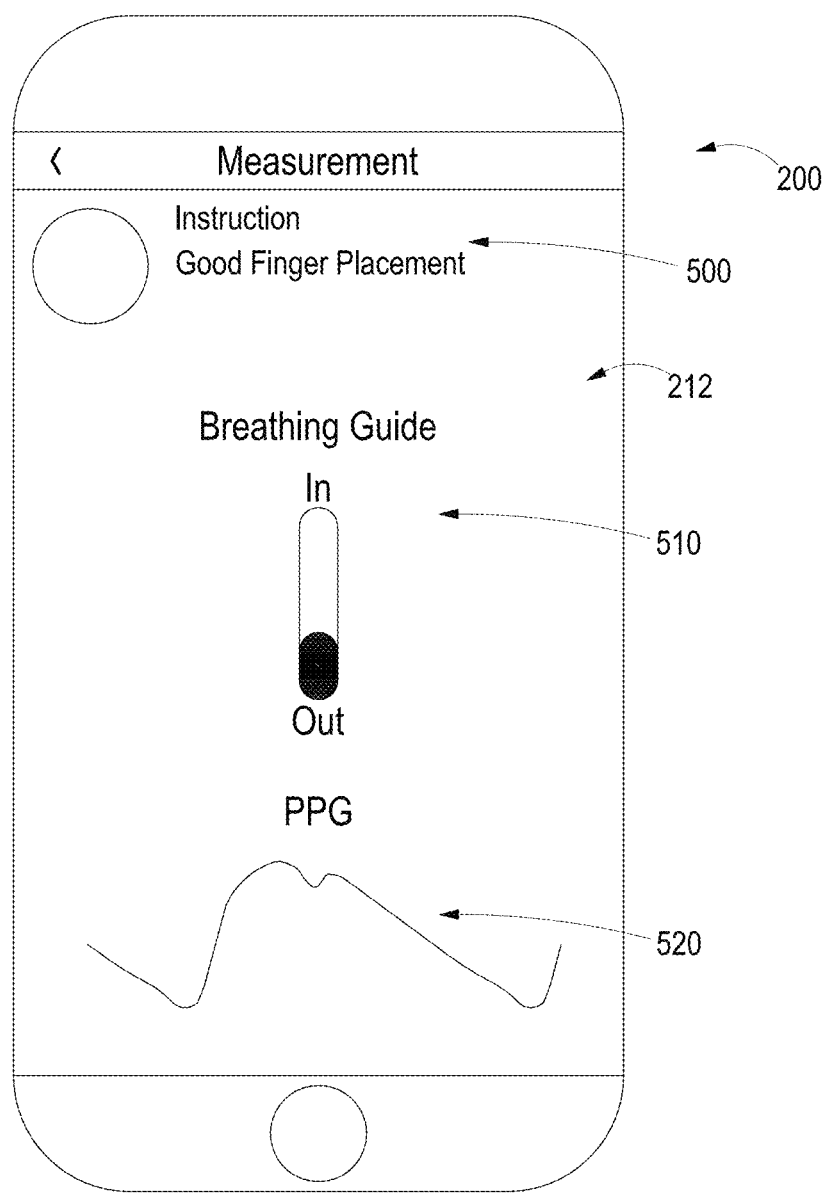
FIG. 5 illustrates the front view of the smartphone of FIGS. 2-4 with the display screen of the smartphone showing instructions to a user.

The system and method first verify that the smartphone 200 (FIGS. 2-4) is obtaining valid PPG readings via the camera lens 210. If so, the system and method display a message 500 that the user's finger is positioned correctly as shown in FIG. 5. If not, the system and method display a message (not shown) requesting the user to reposition his or her fingertip on the camera lens. As further shown in FIG. 5, when the system and method verify that the PPG readings are acceptable, the system and method display a breathing guide 510 to instruct the user to inhale and exhale at prescribed times. While the user is breathing as instructed, the system and method obtain a PPG reading over multiple heartbeats. In the illustrated embodiment, the system and method also display a graphical representation 520 of the PPG waveform obtained via the camera lens.

After instructing the user to breathe for about 10 to 30 seconds while the user is in a first postural position (e.g., seated), the system and method instruct the user to change postural positions (e.g., to stand up quickly to a fully upright position) while maintaining the fingertip over the camera lens. The user continues to breathe as instructed for another 10 to 30 seconds while the system and method obtain a PPG reading over multiple heartbeats. In certain embodiments, the user is instructed to breathe for approximately 20 seconds for each stage of the test.

When the system and method complete the PPG reading while the user is in the second postural position (e.g., standing), the system and method then determines the user's first (e.g., seated) HRV value and the user's second (e.g., standing) HRV value based on the respective PPG readings. The system and method calculate the user's hydration state by comparing the two HRV values as described below.

As discussed above, in the illustrated embodiment, a baseline HRV value is first determined for a user. A method 600 for obtaining the baseline HRV value is illustrated by a flowchart in FIGS. 6A and 6B. In an initial step 610 of the method, the user is directed to obtain a seated HRV reading by following the steps described above with respect to FIGS. 4 and 5. The first step produces a first HRV value when the user is in a first postural position. In the illustrated embodiment, the first postural position is a seated position. In other embodiments, the first postural position may be a supine position or a reclining position.

In the illustrated embodiment, the first HRV value is identified as pNN50. The value pNN50 is a commonly used term to quantify the variations in the RR-intervals. The value pNN50 is first determined by identifying the number of pairs of successive RR-intervals that differ from each other by more than 50 milliseconds to obtain a value NN50. The value NN50 is divided by the total number of pairs of successive RR-intervals in a measurement procedure to determine the percentage of successive RR-intervals that differ by more than 50 milliseconds. Accordingly, the value pNN50 is a value representing HRV. Other parameters for determining HRV may also be used.

After obtaining the first HRV value, the method 600 directs the user to change from the first postural position to a second postural position. In the illustrated embodiment, the user is prompted to stand up abruptly from the original seated position to a standing position. In other embodiments, the user may rise from a supine position or from a reclining position. The user changes positions while continuing to maintain the smartphone in the measurement configuration as illustrated by a step 612. As illustrated by a step 614, the method obtains a second HRV value (e.g., a second pNN50 value) while the user is in the second postural position.

The method 600 then performs a step 616 wherein the method determines a value HRV_DIF, which is the difference between the first HRV value and the second HRV value. The method then advances to a decision step 620.

In the decision step 620, the method 600 compares the calculated HRV difference value (HRV_DIF) from the step 616 to an acceptable HRV_DIF value to provide a first determination whether the user is likely to be properly hydrated. In the illustrated example, an acceptable value of HRV_DIF is 9 or less. Accordingly, in the decision step 620, the method determines whether the difference value is greater than 9.

If the HRV_DIF value is greater than 9 in the decision step 620, the method proceeds to a step 622 wherein the user is instructed to consume liquids to increase the user's level of hydration. In a step 624, the user is instructed to return in one day for additional testing. The one-day delay in the testing method is represented by a delay step 626, which returns the method to the initial step 610.

If the HRV_DIF value is not greater than 9 in the decision step 620, the method 600 of FIGS. 6A and 6B advances to a step 630 in which the user is prompted to respond to a first question in a series of subjective questions regarding the user's condition related to possible dehydration. In the step 630, the method requests the user to respond to the following subjective question:

Are you experiencing excessive thirst? {On a scale of 1-5 with 1 being no thirst and 5 being excessive thirst}

The method 600 advances to a step 632 to apply a weighting factor associated with the user having the selected thirst value to generate a first weighted value. The first weighted value is added to a weighted total, which is initiated to 0 at the start of the test. The method then advances to a step 634. In various embodiments, one or more of the values 1-5 selected by the user may be associated with one or more thresholds. For example, in a binary decision configuration a value of 1 or 2 may be associated with a "NO" value, whereas a value of 3-5 may be associated with a "YES" value. Additionally or alternatively, a value of 1 or 2 may be associated with a not dehydrated determination, a value of 3 may be associated with a mild dehydration determination, and a value of 4 or 5 may be associated with a moderate or severe dehydration determination. One or more value determinations or ranges of the selected value provided by the user may be predetermined, dynamically determined, or a combination thereof. For example, the system may initially associate values of 1 or 2 to be a no dehydration result and values of 3 or more to be a dehydrated result. Over time it may be determined by systems consistent with the present disclosure that a value in the range of 1-3 should be associated with a no dehydration result and that a value of 4 or 5 should be associated with a dehydrated result. The system may automatically and/or dynamically adjust the method accordingly. One or more additional correlations may be determined or inferred in association with the selected value, for example based at least in part upon historical data of the user and/or historical data of one or more other others.

It may be determined whether the user's selected thirst value satisfies a dehydration threshold. The dehydration threshold may include a value above which it is determined that the user is currently experiencing excessive thirst or is dehydrated in the manner described above. For example, a user selection of a value of 3 or above on a 1-5 scale of thirst may cause a first response value to be generated or determined. Furthermore, two or more thresholds may be used with respect to the same user value, for example in the case of an upper threshold and a lower threshold.

In the step 634, the method requests the user to respond to the following question (based on the second postural position being a standing position):

Did you feel lightheaded upon standing {YES or NO}

If the response to the question in the step 634 is YES, the method 600 advances to a step 636 to apply a weighting factor associated with the user being lightheaded to generate a second weighted value, which is added to the weighted total. The method then advances to a step 640. If the response to the question in the step 634 is NO, the method advances directly to the step 640 without generating the second weighted value to add to the weighted total.

In the step 640, the method requests the user to respond to the following question:

Are you experiencing nausea, vomiting or reduced oral intake? {YES or NO}

If the response to the question in the step 640 is YES, the method 600 advances to a step 642 to apply a weighting factor associated with the user experiencing nausea, vomiting or reduced oral intake to obtain a third weighted value. The method then advances to a step 650 (FIG. 6B). If the response to the question in the step 640 is NO, the method advances directly to the step 650 without generating the third weighted value and adding the third weighted value to the weighted total.

In the step 650 (FIG. 6B), the method 600 requests the user to respond to the following question:

What is color of your urine? {Clear, Pale, Light Yellow, Dark Yellow, Brown}

The user responds with one of the five colors, and the method 600 advances to a selected step based on the user's response. If the color is clear, the method advances to a step 660. If the color is pale, the method advances to a step 662. If the color is light yellow, the method advances to a step 664. If the color is dark yellow, the method advances to a step 666. If the color is brown, the method advances to a step 668.

In the step 660, the method 600 adds a weighted value corresponding to the presence of clear urine to the weighted total and then advances to a decision step 670. In the step 662, the method adds a weighted value corresponding to the presence of pale urine to the weighted total and then advances to the decision step 670. In the step 664, the method adds a weighted value corresponding to the presence of light-yellow urine to the weighted total and then advances to the decision step 670. In the step 666, the method adds a weighted value corresponding to the presence of dark yellow urine to the weighted total and then advances to the decision step 670. In the step 668, the method adds a weighted value corresponding to the presence of brown urine to the weighted total and then advances to the decision step 670. The weighted values for each of the five color choices may all be different in certain embodiments. In other embodiments, the five color choices may be grouped such that the colors clear, pale and light yellow may be accorded a first common weight and the colors dark yellow and brown may be accorded a second common weight.

In the step 670, the method 600 compares the weighted total to a threshold value to determine whether the weighted total exceeds the threshold value. The threshold value is selected to represent the maximum weighted total value of a typical user who is in a state of adequate hydration. If the weighted total exceeds the threshold value, the method proceeds to the step 622 (FIG. 6A) wherein the user is instructed to consume liquids to increase the user's level of hydration. In the step 624, the user is instructed to return in one day for additional testing. The method returns to the initial step 610 via the one-day delay step 626.

If the weighted total does not exceed the threshold value in the decision step 670, the method 600 advances to a step 672 wherein the method saves the HRV_DIF value determined in the step 616 as a value X[N] wherein N represents the number of saved values for the user in the current test procedure.

After saving the HRV_DIF value in the step 672, the method 600 advances to decision step 674 wherein the method determines whether the currently saved value is a first saved value (X[1]), a second saved value (X[2]) or a third saved value (X[3]). If the currently saved value is the first saved value or the second saved value, the method advances to a step 676 wherein the user is instructed to remain hydrated. The method advances to the step 624 (FIG. 6A) wherein the user is instructed to perform the test again in one day. The method then returns to the initial step 610 via the one-day delay step 626. The testing over a plurality of days (e.g., a rolling average over N days, for example seven or thirty days) enables the method to obtain HRV_DIF values that represent a range of acceptable hydration.

If the currently saved value is the third saved value, the method 600 advances from the decision step 674 to a step 680 wherein a baseline value is calculated by adding the N saved values (e.g., a rolling average of any number of days may be used, for example a seven-day or thirty-day average) and dividing by the number of saved values to obtain an average of the saved HRV_DIF values as follows:

$$\text{BASELINE} = \frac{X[1] + X[2] + \ldots + X[N]}{N}$$

In a step 682, the method 600 stores the calculated baseline value in the user's smartphone 200 (FIGS. 2-5) or other smart device to be used for further self-testing as described below. The method 600 then exits.

FIGS. 7A and 7B illustrates a flowchart 700 of an alternative version of a test method for determining a baseline differential HRV value for a user. Many of the steps of the method 700 correspond to the above-described steps of the method 600.

In an initial step 710 of the method 700, the user is directed to obtain a first HRV value in a first postural position (e.g., seated) by following the steps described above with respect to FIGS. 4 and 5.

After obtaining the first HRV value, the method 700 directs the user to change to a second postural position while continuing to maintain the smartphone in the measurement configuration as illustrated by a step 712. The method obtains a second HRV value while the user is breathing in the second postural position, as illustrated by a step 714.

The method 700 then performs a step 716 wherein the method 700 determines a value HRV_DIF, which is the difference between the first HRV value and the second HRV value. The method then advances to a decision step 720.

In a decision step 720, the method 700 compares the calculated HRV difference value (HRV_DIF) from the step 716 to an acceptable HRV_DIF value to provide a first determination whether the user is likely to be properly hydrated. In the illustrated example, an acceptable value of HRV_DIF is 9 or less. Accordingly, in the decision step 720, the method determines whether the difference value is greater than 9.

If the HRV_DIF value is greater than 9 in the decision step 720, the method 700 proceeds to a step 722 wherein the user is instructed to consume liquids to increase the user's level of hydration. In a step 724, the user is instructed to return in one day for additional testing. The one-day delay in the testing method is represented by a delay step 726, which returns the method to the initial step 710.

If the HRV_DIF value is not greater than 9 in the decision step 720, the method 700 of FIGS. 7A and 7B advances to a step 730 in which the user is prompted to respond to a first question in a series of subjective questions regarding the user's condition related to possible dehydration. In the step 730, the method requests the user to respond to the following subjective question:

Are you experiencing excessive thirst? {On a scale of 1-5 with 1 being no thirst and 5 being excessive thirst}

The method 700 advances to a step 732 wherein the method increments a value representing the number of responses having a value greater than 1. The value is initiated to 0 at the start of the test. A weighting factor is optionally associated with the user having the selected thirst value to generate a first weighted value. The first weighted value is added to a weighted total, which is initiated to 0 at the start of the test. The method then advances to a step 734. Similar to the method as described above with reference to FIG. 6, in various embodiments one or more of the values 1-5 selected by the user may be associated with one or more thresholds. For example, in a binary decision configuration a value of 1 or 2 may be associated with a "NO" value, whereas a value of 3-5 may be associated with a "YES" value. Additionally or alternatively, a value of 1 or 2 may be associated with a not dehydrated determination, a value of 3 may be associated with a mild dehydration determination, and a value of 4 or 5 may be associated with a moderate or severe dehydration determination. One or more value determinations or ranges of the selected value provided by the user may be predetermined, dynamically determined, or combination thereof. For example, the system may initially associate values of 1 or 2 to be a no dehydration result and values of 3 or more to be a dehydrated result. Over time it may be determined by systems consistent with the present disclosure that a value in the range of 1-3 should be associated with a no dehydration result and that a value of 4 or 5 should be associated with a dehydrated result. The system may automatically and/or dynamically adjust the method accordingly. One or more additional correlations may be determined or inferred in association with the selected value, for example based at least in part upon historical data of the user and/or historical data of one or more other others.

It may be determined whether the user's selected thirst value satisfies a dehydration threshold. The dehydration threshold may include a value above which it is determined that the user is currently experiencing excessive thirst. For example, a user selection of a value of 3 on a 1-5 scale of thirst may cause a first response value to be generated or determined. Furthermore, two or more threshold may be used with respect to the same user value, for example in the case of an upper threshold and a lower threshold. One or more thresholds may be added or modified based at least in part upon a subset or data (either directly from historical or population data or as inferred from at least one source of historical or population data) and/or one or more weighted values.

In the step 734, the method requests the user to respond to the following question (based on the second postural position being a standing position):

Did you feel lightheaded upon standing {YES or NO}

If the response to the question in the step 734 is YES, the method 700 advances to a step 736 wherein the method increments the value representing the number of YES responses. The method then advances to a step 740. If the response to the question in the step 734 is NO, the method advances directly to the step 740 without incrementing the value representing the number of YES responses.

In the step 740, the method 700 requests the user to respond to the following question:

Are you experiencing nausea, vomiting or reduced oral intake? {YES or NO}

If the response to the question in the step 740 is YES, the method 700 advances to a step 742 wherein the method increments the value representing the number of YES responses. The method then advances to a step 750 (FIG. 7B). If the response to the question in the step 740 is NO, the method advances directly to the step 750 without incrementing the value representing the number of YES responses.

In the step 750 (FIG. 7B), the method 700 requests the user to respond to the following question:

What is color of your urine? {Clear, Pale, Light Yellow, Dark Yellow, Brown}

The user responds with one of the five colors; and the method 700 advances to a decision step 752 to process the user's response. If the user responds that the urine is dark yellow or brown, the method advances to a step 754 wherein the method increments the value representing the number of YES responses. The method then advances to a step 760. If the response to the question in the step 752 is NO, the method advances directly to the step 760 without incrementing the value representing the number of YES responses.

In the step 760, the method 700 determines whether the number of YES responses is greater than 2. Two or more YES responses suggest that the user may be in a state of inadequate hydration. If the number of YES responses is greater than 2, the method proceeds to the step 722 (FIG. 7A) wherein the user is instructed to consume liquids to increase the user's level of hydration. In the step 724, the user is instructed to return in one day for additional testing. The method returns to the initial step 710 via the one-day delay step 726.

If the number of YES responses does not exceed 2 in the step 760, the method 700 advances to a step 762 wherein the method saves the pNN50dif value determined in the step 716 as a value X(N) wherein N represents the number of saved values for the user in the current test procedure.

After saving the HRV_DIF value in the step 762, the method 700 advances to decision step 764 wherein the method determines whether the currently saved value is a first saved value (X[1]), a second saved value (X[2]) or a third saved value (X[3]). If the currently saved value is the first saved value or the second saved value, the method advances to a step 766 wherein the user is instructed to remain hydrated. The method advances to the step 724 (FIG. 7A) wherein the user is instructed to perform the test again in one day. The method then returns to the initial step 710 via the one-day delay step 726. The testing over a plurality of days enables the method to obtain HRV_DIF values that represent a range of acceptable hydration.

If the currently saved value is the third saved value, the method 700 advances from the decision step 764 to a step 770 wherein a baseline value is calculated by adding the plurality of saved values (e.g., a rolling average of N days, or example a seven or thirty day rolling average) and dividing by the number of saved values to obtain an average of the saved HRV_DIF values as follows:

$$\text{BASELINE} = \frac{X[1] + X[2] + \ldots + X[N]}{N}$$

In a step 772, the method 700 stores the calculated baseline value in the user's smartphone 200 (FIGS. 2-5) or other smart device to be used for further self-testing as described below. The method then exits.

After the baseline is established by the method 600 of FIGS. 6A and 6B or by the method 700 of FIGS. 7A and 7B, the user can use the smartphone 200 or other smart device to obtain a current evaluation of the user's hydration as often as the user desires. As described below, each hydration evaluation can be completed in 60 to 90 seconds with little effort on the part of the user other than sitting for approximately 10-30 seconds and breathing as instructed; and then rising rapidly to a standing position and breathing as instructed for another 10-30 seconds. The hydration evaluation is performed by a method 800 illustrated as a flowchart in FIGS. 8A and 8B.

As described above with respect to the method 600 or the method 700, a baseline HRV_DIF value (BASELINE) is stored in the smartphone or other smart device. The stored baseline HRV_DIF value is determined by the number of days of successful testing when the user is hydrated. The method 800 of FIGS. 8A and 8B uses the stored baseline HRV_DIF value and a current HRV_DIF value to determine a daily score as follows.

In an initial step 810 of the method 800, the user is directed to obtain a first HRV value by following the steps described above with respect to FIGS. 3, 4 and 5. As described above, the first step produces a first HRV value while the user is in a first postural position (e.g., a seated or supine position).

After obtaining the first HRV value, a step 812 of the method 800 directs the user to change to a second postural position (e.g., standing) while continuing to maintain the smartphone in the measurement configuration. In a step 814, the method obtains a second HRV value while the user is in the second postural position.

In a step 816, the method 800 determines and HRV_DIF value, which is the difference between the first HRV value and the second HRV value. The HRV DIF value obtained in this self-testing method is also referred to as the "daily score."

After obtaining the daily score value (e.g., HRV_DIF), the method 800 advances to a step 820, wherein the method calculates a "hydration score." Calculation of the hydration score is addressed in more detail below with reference to FIG. 11. In embodiments where there is sufficient historical user information to calculate a baseline hydration value, the hydration score may be calculated as the difference between the previously stored baseline value and the daily score as follows:

$$Hydration_{score} = Baseline - Daily\_Score$$

If, however, insufficient historical user data is known, the process may look to a comparison of the user's answers to subjective questions and/or population data associated with other users, with the subjective question answers and/or population data are compared to the first HRV value and the second HRV value to determine a hydration score, as described in more detail below with reference to FIG. 11. One or more sets of hydration status information may be stored at the electronic device (e.g., smartphone 200).

After determining the hydration score in the step 820, the method 800 determines whether the hydration score is greater than 9 in a step 822. If the hydration score is greater than 9, the method 800 proceeds to a severe hydration display step 830 (FIG. 8B) wherein the method displays a red status symbol on the screen of the smartphone 200 or other smart device. The user is instructed to take prompt steps in response to the red status symbol to increase fluid intake to increase hydration.

If the hydration score is no more than 9 in the step 822, the method 800 requests the user to respond to the three subjective questions as previously described.

In a step 840, the method 800 of FIGS. 8A and 8B requests the user to respond to the following subjective question:

Are you experiencing excessive thirst? {On a scale of 1-5 with 1 being no thirst and 5 being excessive thirst}

The method 800 advances to a step 842 wherein the method increments a value representing the number of responses having a value greater than 1. The number of responses having a value greater than 1 is initiated to 0 at the start of the test. A weighting factor is optionally associated with the user having the selected thirst value to generate a first weighted value. The first weighted value is added to a weighted total, which is initiated to 0 at the start of the test. The method then advances to a step 844.

In the step 844, the method 800 requests the user to respond to the following question (based on the second postural position being a standing position):

Did you feel lightheaded upon standing {YES or NO}

If the response to the question in the step 844 is YES, the method 800 advances to a step 846 wherein the method increments the value representing the number of YES responses. The method then advances to a step 850. If the response to the question in the step 844 is NO, the method advances directly to the step 850 without incrementing the value representing the number of YES responses.

In the step 850, the method 800 requests the user to respond to the following question:

Are you experiencing nausea, vomiting or reduced oral intake? {YES or NO}

If the response to the question in the step 850 is YES, the method 800 advances to a step 852 wherein the method increments the value representing the number of YES responses. The method then advances to a step 860 (FIG. 7B). If the response to the question in the step 850 is NO, the method advances directly to the step 860 without incrementing the value representing the number of YES responses.

In the step 860 (FIG. 8B), the method 800 prompts the user to enter the color of the user's urine (e.g., clear, pale, light yellow, dark yellow or brown). The method then proceeds to a decision process beginning with a decision step 862.

In the decision step 862, the method determines whether the hydration score determined in the step 820 is greater than 9. If the hydration score is not greater than 9, the method proceeds from the decision step 862 to a decision step 870 wherein the method determines whether the number of YES responses to the three subjective questions is greater than 2. If the number of YES responses is not greater than 2, the method proceeds from the decision step 870 to a decision step 872 wherein the method determines whether the urine color entered by the user is either dark yellow or brown. If the urine color is not dark yellow or brown, the method proceeds from the decision step 872 to a satisfactory hydration display step 874 wherein the method displays a green status symbol on the screen of the smartphone 200 or other smart device.

If the urine color is dark yellow or brown, the method proceeds from the decision step 872 to a moderate dehydration display step 876 wherein the method displays a yellow status symbol on the screen of the smartphone 200 or other smart device to indicate to the user that the user should be increasing fluid intake to increase hydration.

If the number of YES responses to the three subjective questions is greater than 2, the method 800 proceeds from the decision step 870 to a decision step 880 wherein the method determines whether the urine color entered by the user is either dark yellow or brown. If the urine color is not dark yellow or brown, the method proceeds from the decision step 880 to the moderate dehydration display step 876 wherein the method displays a yellow status symbol on the screen of the smartphone 200 or other smart device to indicate to the user that the user should be increasing fluid intake to increase hydration.

If the urine is dark yellow or brown, the method 800 proceeds from the decision step 880 to the severe dehydration display step 830 wherein the method displays the red status symbol on the screen of the smartphone 200 or other smart device to indicate to the user that the user should take prompt steps to increase hydration.

If the method 800 determines that the hydration score is greater than 9 in the decision step 862, the method proceeds from the decision step 862 to a decision step 890 wherein the method determines whether the urine color entered by the user is either dark yellow or brown. If the urine color is not dark yellow or brown, the method proceeds from the decision step 890 to the moderate dehydration display step 876 wherein the method displays the yellow status symbol on the screen of the smartphone 200 or other smart device to indicate to the user that the user should be increasing fluid intake to increase hydration.

If the urine is dark yellow or brown, the method 800 proceeds from the decision step 890 to the severe dehydration display step 830 wherein the method displays the red status symbol on the screen of the smartphone 200 or other smart device to indicate to the user that the user should take prompt steps to increase hydration.

After displaying the appropriate green, yellow or red status symbol on the smartphone 200, the method 800 exits and awaits restarting for a new test. As indicated above, the method requires no more than 90 seconds to perform the steps of the test.

The method 800 of FIGS. 8A and 8B may also be implemented using weighted values for the three subjective questions and the five urine colors as described above with respect to the method 600 of FIGS. 6A and 6B.

The methods 600, 700 and 800 are described above with respect to the flowcharts illustrated in FIGS. 6A and 6B, FIGS. 7A and 7B and FIGS. 8A and 8B, respectively. The methods may also be implemented in other manners. For example, the first HRV value, the second HRV value, the baseline value, the responses to the subjective questions and the urine colors may also be provided as entries to a lookup table, which provides a selected output based on the combination of the entries.

As the methods 600, 700 and 800 are used in the field, data from multiple users with different physical characteristics may be accumulated. When sufficient data are accumulated, the baseline for a user may be determined based on the user's physical characteristics and the baseline data from prior users with similar physical characteristics. Other features, such as, for example, automatically detecting postural changes (e.g., a user transitioning from a seated position to a standing position) may also be incorporated into the above-described methods.

The subjective questions and the urine color evaluation may not be required in certain embodiments of the daily self-test method illustrated in FIGS. 8A and 8B. For example, FIG. 9 illustrates an embodiment of a daily self-test method 900 that does not require the user to respond to questions.

The method 900 of FIG. 9 uses the stored baseline HRV_DIF value and a current HRV_DIF value to determine a daily score as follows.

In an initial step 910 of the method 900, the user is directed to obtain a first HRV value by following the steps described above with respect to FIGS. 3, 4 and 5. As described above, the first step produces a first HRV value while the user is in a first postural position (e.g., a seated or supine position).

After obtaining the first HRV value, a step 912 of the method 900 directs the user to change to a second postural position (e.g., standing) while continuing to maintain the smartphone in the measurement configuration. In a step 914, the method obtains a second HRV value while the user is in the second postural position.

In a step 916, the method 900 determines and HRV_DIF value, which is the difference between the first HRV value and the second HRV value. The HRV_DIF value obtained in this self-testing method is also referred to as the "daily score."

After obtaining the daily score value (e.g., HRV_DIF), the method 900 advances to a step 920, wherein the method calculates a "hydration score." Calculation of the hydration score is addressed in more detail below with reference to FIG. 11. In embodiments where there is sufficient historical user information to calculate a baseline hydration value, the hydration score may be calculated as the difference between the previously stored baseline value and the daily score as follows:

$$\text{Hydration}_{score} = \text{Baseline} - \text{Daily\_Score}$$

If, however, insufficient historical user data is known, the process may look to a comparison of the user's answers to subjective questions and/or population data associated with other users, with the subjective question answers and/or population data are compared to the first HRV value and the second HRV value to determine a hydration score, as described in more detail below with reference to FIG. 11. One or more sets of hydration status information may be stored at the electronic device (e.g., smartphone 200).

After determining the hydration score in the step 920, the method 900 determines whether the hydration score is greater than 9 in a decision step 922. If the hydration score is greater than 9, the method 900 proceeds to a severe hydration display step 924 wherein the method displays a red status symbol on the screen of the smartphone 200 or other smart device. The user is instructed to take prompt steps in response to the red status symbol to increase fluid intake to increase hydration.

If the hydration score is not greater than 9 in the decision step 922, the method 900 proceeds to a decision step 930 to determine whether the hydration score is greater than 6. If the hydration score is greater than 6, the method proceeds to a moderate hydration display step 932 wherein the method displays a yellow status symbol on the screen of the smartphone or other smart device.

If the hydration score is not greater than 6 in the decision step 930, the method 900 proceeds to a hydrated display step 940 wherein the method displays a red status symbol on the screen of the smartphone or other smart device.

The threshold numbers 9 and 6 for the daily score in the foregoing description are examples of threshold numbers for one user. As information is gathered for a user, the threshold numbers may be adjusted for that user in accordance with a relationship established between hydration and the daily score.

FIG. 10 illustrates an exemplary embodiment of a process for positioning a person's finger for use with a photoplethysmography (PPG) measurement device according to aspects of the present disclosure. The process 1000 begins at an operation 1002 where the camera lens 210 (e.g., camera) and light source (e.g., LED light source) of the smartphone 200 is activated. Although described with reference to a smartphone 200, it should be appreciated that any electronic device having an element such as a camera to obtain an image and a light source to illuminate an image capture area may be used without departing from the spirit and scope of the present disclosure. An image of the tip 222 of the person's index finger 220 may be captured at an operation 1004. Additionally or alternatively, an image of a different finger or of a different portion of the person's body may be captured for use herewith. It is then determined at an operation 1006 whether the person's fingertip is in an acceptable position for PPG reading.

If the result of operation 1006 is negative, the process continues to an operation 1008 where the person is selectively notified of a finger position issue (e.g., via one or more visual and/or audible alerts) and the person may be requested to reposition his or her tip 222 of an index finger for reading. In various embodiments, the person may be provided with a visual or audible guide on proper fingertip positioning, such as a visual overlay on a display element of the smartphone 200 or audible instructions. The process then continues to an operation 1010 where an image of the repositioned fingertip is obtained. The process then returns to operation 1006 where it is determined whether the person's fingertip is in an acceptable position for PPG reading.

If it is determined that the person's fingertip is in an acceptable position at operation 1006, the process continues to an operation 1012 where at least one PPG reading is obtained from the person using the camera and the lighting element. At least a portion of the PPG reading may be analyzed at an operation 1014 in a manner consistent with the present disclosure. The PPG reading or information relating to the PPG reading may be selectively stored at the smartphone 200 at an operation 1016 and the process may then end for a single PPG reading. In a scenario where multiple PPG readings are to be obtained, the process may selectively return to operation 1002.

Implementations consistent with the process of FIG. 10 may assist in overcoming shortfalls in existing technology. For example, improper fingertip positioning can lead to bad measurement data and thus invalid PPG data and may have downstream effects on historical data or trend analysis. However, a camera lens 210 or light source of a smartphone 200 alone is incapable of determining proper measurement parameters. Thus, providing proper instruction to both the smartphone 200 and to the person using the smartphone 200 regarding fingertip positioning can provide solutions not previously capable of resolution and may provide vastly more precise data and enable a faster measurement process where measured data is assumed to be correct when measured in a proper positioning. As such, implementations consistent with the present disclosure may provide a technical solution to a problem that exists solely in the technological space—i.e., by resolving a problem with the electronic capture of proper measurement data which is not capable of being obtained manually.

FIG. 11 illustrates an exemplary embodiment of a process for determining a hydration score for a user according to aspects of the present disclosure. The process 1100 begins at an operation 1102 where a user's baseline history is examined. Examining the baseline history may include determining a number of baseline hydration values, HRV values, or other testing data associated with a particular user and associated with the user's baseline or trending hydration status. It is determined at an operation 1104 whether sufficient baseline history exists for the user. Sufficient baseline history may include a number of historical baseline hydration values above a predetermined or dynamically determined threshold, a number of historical HRV values, historical testing data associated with the user, and/or population data of other users having similar historical and/or current information, either alone or in combination. A BASELINE data value may be obtained directly as from historical data or may be calculated based at least on part upon information included in the baseline history.

If it is determined at operation 1104 that sufficient baseline history exists, the process continues to an operation 1106 where a hydration score value HYDRATION_SCORE may be determined according to the equation:

$$HYDRATION\_SCORE = DAILY\_SCORE - BASELINE$$

After calculating the value of HYDRATION_SCORE the process 1100 then returns to step 822 (FIG. 8A) or 922 (FIG. 9A).

If it is determined at operation 1104 that insufficient baseline history exists, the process continues to an operation 1108 where answers to subjective questions provided by the user and/or population data of other users are examined and compared to the first HRV and second HRV values. The process then continues to an operation 1110 where a value for HYDRATION_SCORE is determined based at least in part upon a comparison of the user's answers to the subjective questions and/or population data to the first HRV and second HRV values. The process then returns to step 822 (FIG. 8A), 922 (FIG. 9A).

The previous detailed description has been provided for the purposes of illustration and description. Thus, although there have been described particular embodiments of a new and useful invention, it is not intended that such references be construed as limitations upon the scope of this invention except as set forth in the following claims.

What is claimed is:

1. A method for determining a hydration status of a person comprising:
    obtaining at least one photoplethysmography (PPG) reading from the person using a camera and associated lighting source of an electronic device;
    prompting the person to breathe at a first selected pace for a first selected duration while in a first postural position;
    measuring the person's heart rate variability (HRV) during the first selected duration to obtain a first HRV value;
    prompting the person to change from the first postural position to a second postural position;
    prompting the person to breathe at a second selected pace for a second selected duration while in the second postural position;
    measuring the person's HRV during the second selected duration to obtain a second HRV value;
    calculating a difference between the first HRV value and the second HRV value to generate a daily score;

calculating a baseline value for the person according to historical HRV data and storing the baseline value at the electronic device; and subtracting the baseline value from the daily score to obtain a hydration score.

2. The method as defined in claim 1, wherein the first postural position is the person seated; and the second postural position is the person standing.

3. The method as defined in claim 1, wherein the first postural position is the user in a supine position; and the second postural position is the user standing.

4. The method as defined in claim 1, further comprising:
requesting the person to respond to a plurality of subjective questions to produce a corresponding plurality of subjective responses; and
processing the plurality of subjective responses and the daily score to determine whether the person is adequately hydrated.

5. The method as defined in claim 4, wherein the plurality of subjective questions comprises:
asking whether the person is experiencing excessive thirst to cause the person to input a first response;
asking whether the person felt light-headed upon changing from the first postural position to the second postural position to cause the person to input a second response; and
asking whether the person is experiencing nausea, vomiting or reduced oral intake to cause the person to input a third response.

6. The method as defined in claim 5, further comprising:
generating a first response value when the first response is satisfies a dehydration threshold;
generating a second response value when the second response is YES;
generating a third response value when the third response is YES.

7. The method as defined in claim 6, further comprising:
applying a first weighting factor to the first response value;
applying a second weighting factor to the second response value; and
applying a third weighting factor to the third response value.

8. The method as defined in claim 5, further comprising:
asking the person to identify the color of the person's urine by selecting one of clear, pale, light yellow, dark yellow or brown; and
determining the person's hydration state based on the first response, the second response, the third response, and the identified color of the person's urine.

9. The method as defined in claim 1, wherein:
the first time duration is between 10 and 30 seconds; and
wherein the second time duration is approximately the same as the first time duration.

10. The method as defined in claim 1, wherein the baseline value is determined by:
directing the person to perform a plurality of tests, wherein within each test, the method comprises:
prompting the person to breathe at a first selected pace for a first selected duration while in the first postural position;
measuring the person's heart rate variability (HRV) during the first selected duration to obtain the first HRV value;
prompting the person to change from the first postural position to the second position;
prompting the person to breathe at a second selected pace for a second selected duration while in the second postural position;
measuring the person's HRV during the second selected duration to obtain the second HRV value;
calculating a difference between the first HRV value and the second HRV value to generate an HRV difference value;
determining whether the HRV difference value is greater than a maximum value;
if the HRV difference value is greater the maximum value, prompting the person to hydrate and to retake the test later;
if the HRV difference value is not greater than the difference value, the method further performing the steps of:
requesting the person to respond to a plurality of subjective questions to produce a corresponding plurality of subjective responses; and
processing the plurality of subjective responses to determine whether to save the HRV difference value or to prompt the user to retake the test later; and
averaging the saved HRV difference values to generate the baseline value.

11. The method as defined in claim 10, wherein the method determines whether to save the HRV difference value by counting a number of YES responses.

12. The method as defined in claim 11, wherein the subjective questions comprise:
asking whether the person is experiencing excessive thirst to cause the person to input a first response;
asking whether the person felt light-headed upon changing from the first postural position to the second postural position to cause the person to input a second response; and
asking whether the person is experiencing nausea, vomiting or reduced oral intake to cause the person to input a third response.

13. The method as defined in claim 12, further comprising:
asking the person to identify a color of the person's urine by selecting one of clear, pale, light yellow, dark yellow or brown; and
determining the person's hydration state based on the plurality of subjective responses and the identified color of the person's urine.

14. The method as defined in claim 10, wherein the plurality of tests comprises seven or thirty tests in which the HRV difference value is saved.

15. A method for determining a hydration status of a person comprising:
obtaining at least one photoplethysmography (PPG) reading from the person using a camera and associated lighting source of an electronic device prompting the person to breathe at a first selected pace for a first selected duration while the person is in a seated position;
measuring the person's heart rate variability (HRV) during the first selected duration to obtain a first HRV value;
prompting the person to rise to a standing position;
prompting the person to breathe at a second selected pace for a second selected duration while the person is in the standing position;
measuring the person's HRV during the second selected duration to obtain a second HRV value;

calculating a difference between the first HRV value and the second HRV value to generate a daily score;

calculating a baseline value for the person according to historical HRV data and storing the baseline value at the electronic device; and subtracting a baseline value from the daily score to obtain a hydration score.

16. A method for determining a hydration status of a person comprising:

obtaining at least one of a photoplethysmography (PPG) measurement value or an electrocardiogram (ECG) measurement value from the person;

transmitting the obtained at least one PPG measurement value or ECG measurement value to an electronic device;

prompting the person to breathe at a first selected pace for a first selected duration while in a first postural position;

measuring the person's heart rate variability (HRV) during the first selected duration to obtain a first HRV value;

prompting the person to change from the first postural position to a second postural position;

prompting the person to breathe at a second selected pace for a second selected duration while in the second postural position;

measuring the person's HRV during the second selected duration to obtain a second HRV value;

calculating a difference between the first HRV value and the second HRV value to generate a daily score;

determining a hydration score based at least in part upon the daily score; and storing one or more sets of hydration status information at the electronic device.

* * * * *